US006333180B1

(12) United States Patent
Farbood et al.

(10) Patent No.: US 6,333,180 B1
(45) Date of Patent: Dec. 25, 2001

(54) BIOPROCESS FOR THE HIGH-YIELD PRODUCTION OF FOOD FLAVOR-ACCEPTABLE JASMONIC ACID AND METHYL JASMONATE

(75) Inventors: Mohamad I. Farbood, State College, PA (US); Robert W. Blocker, Brick, NJ (US); Lynda B. McLean, Matawan, NJ (US); Mark A. Sprecker, Sea Bright, NJ (US); Michael P. McLean, Matawan, NJ (US); Nicolas Kossiakoff, Les Arcs sur Argens (FR); Augustine Yonghwi Kim, Morganville, NJ (US); Myrna Hagedorn, Woodland Park, CO (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/468,134

(22) Filed: Dec. 21, 1999

(51) Int. Cl.[7] ..................................................... C12P 17/02
(52) U.S. Cl. ..................... 435/148; 435/132; 435/136; 435/148; 560/122; 426/534
(58) Field of Search .................................. 435/132, 136, 435/148; 560/122; 426/534

(56) References Cited

U.S. PATENT DOCUMENTS

| 5,681,738 | 10/1997 | Beelman et al. .................. 435/254.1 |
| 6,187,946 | 2/2001 | Fujisawa et al. . | |

FOREIGN PATENT DOCUMENTS

| 279688 | 6/1990 | (DE) . |
| 1286266 | 8/1972 | (GB) . |

OTHER PUBLICATIONS

Jones, *Mycotaxon*, vol. VI, No. 1, pp. 24–26, Jul.–Sep. 1977 entitled: "The Current Taxonomic Status of *Diplodia Gossypina*".
Miersch, et al, I, *Phytochemistry*, vol. 26, No. 4, pp. 1037–1039, 1987 entitled: "(+)–7–Iso–Jasmonic Acid and Related Compounds from *Botryodiplodia Theobromae*".
Miersch, et al, II, *Phytochemistry*, vol. 28, No. 5, pp. 1303–1305, 1989 entitled: "Jasmonic Acid–Like Substances from the Culture Filtrate of *Botryodiplodia Theobromae*".
Husain, et al, *Journal of Natural Products*, vol. 56, No. 11, pp. 2008–2011, Nov. 1993 entitled: "(–)–Jadmonic Acid, A Phytotoxic Substance from *Botryodiplodia Theobromae*: Characterization by NMR Spectroscopic Methods".
Häusler, et al, *ASM News*, vol. 63, No. 10, pp. 551–559 (published by the American Society for Microbiology) entitled: "Microbial Production of Natural Flavors" (specific mention of jasmonic acid production on p. 553).
Eng, et al, *Process Biochemistry*, vol. 33, No. 7, pp. 715–720, 1998 entitled: "Culture conditions for jasmonic acid and biomass production by *Botryodiplodia Theobromae* in submerged fermentation".
Acree, et al, *J. Agric. Food Chem.*, vol. 33, No. 3, 1985, pp. 425–427 entitled: "Odor Thresholds of the Stereoisomers of Methyl Jasmonate."

*Primary Examiner*—Leon B. Lankford, Jr.
(74) *Attorney, Agent, or Firm*—Joseph P. Leightner

(57) ABSTRACT

Described is a bioprocess for the high-yield production of food flavor-acceptable jasmonic acid and methyl jasmonate, as well as a novel jasmonic acid isomer produced thereby and organoleptic uses thereof. The process yields at least 5% of the "cis" isomer defined according the structure:

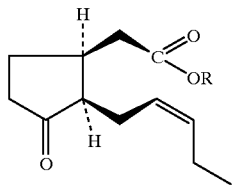

(wherein R is hydrogen or methyl) or at least 5% of the "cis" isomer defined according to the structure:

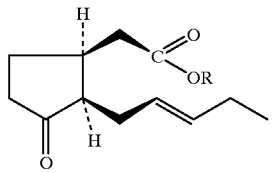

(wherein R is hydrogen or methyl). Compositions containing at least 98% of the isomer having the structure:

with an optical rotation ($\alpha_D^{20}$) of +58° are novel. Compositions containing at least 98% of the isomer having the structure:

with an optical rotation ($\alpha_D^{20}$) of +58° are also novel. The process of our invention comprises the cultivation under aerobic condition of one or more specific strain of *Diplodia gossypina* in a nutrient medium followed either by (1) isolation of the jasmonic acid product or (2) esterification of the jasmonic acid to form methyl jasmonate followed by the isolation of the methyl jasmonate and novel products produced by such process.

23 Claims, 22 Drawing Sheets

FIG. 4-A
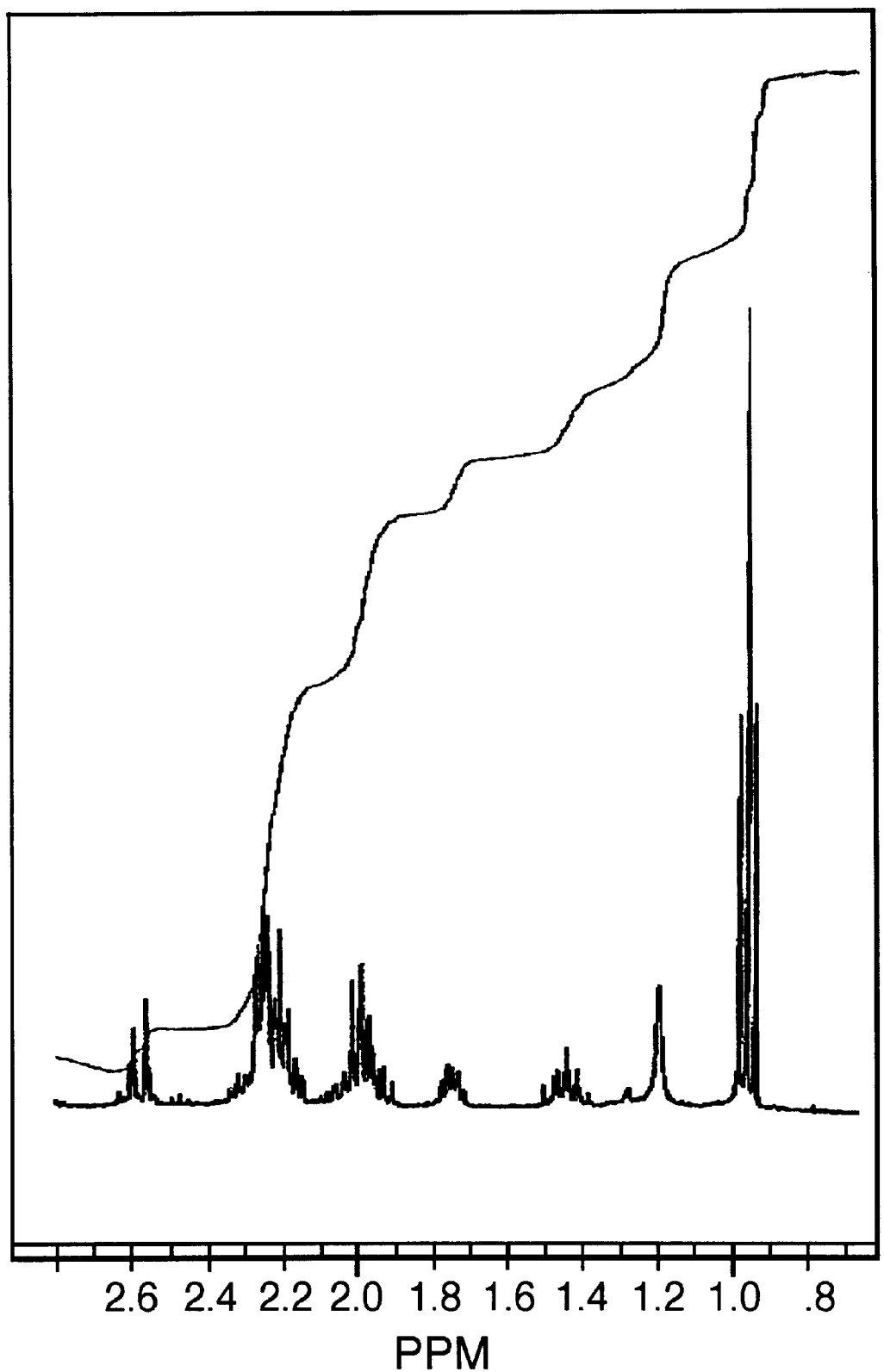

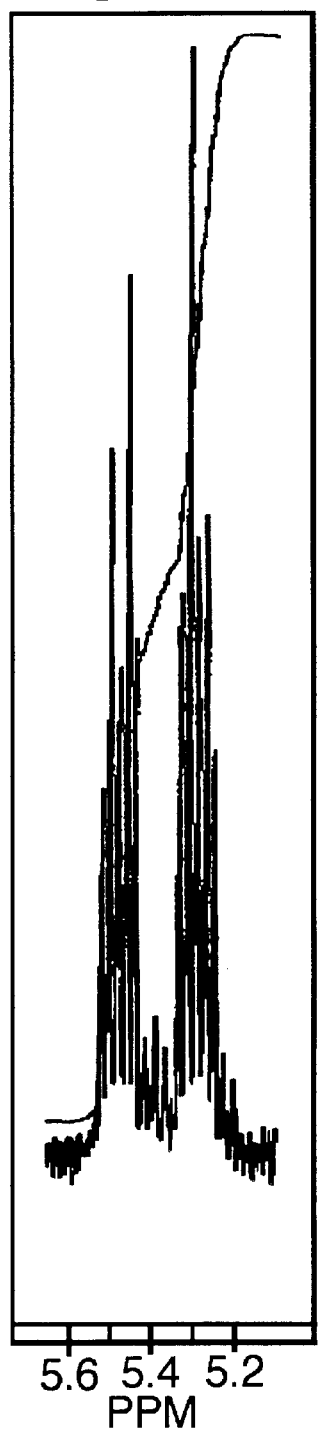
FIG. 4-C
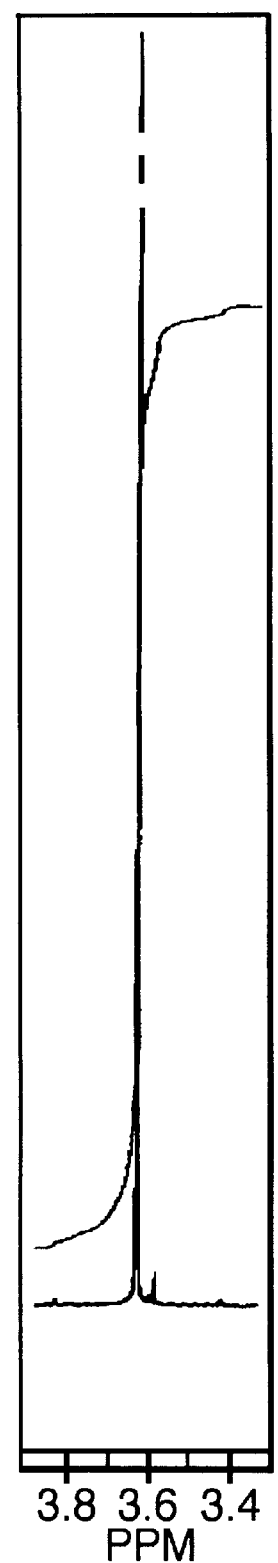
FIG. 4-B

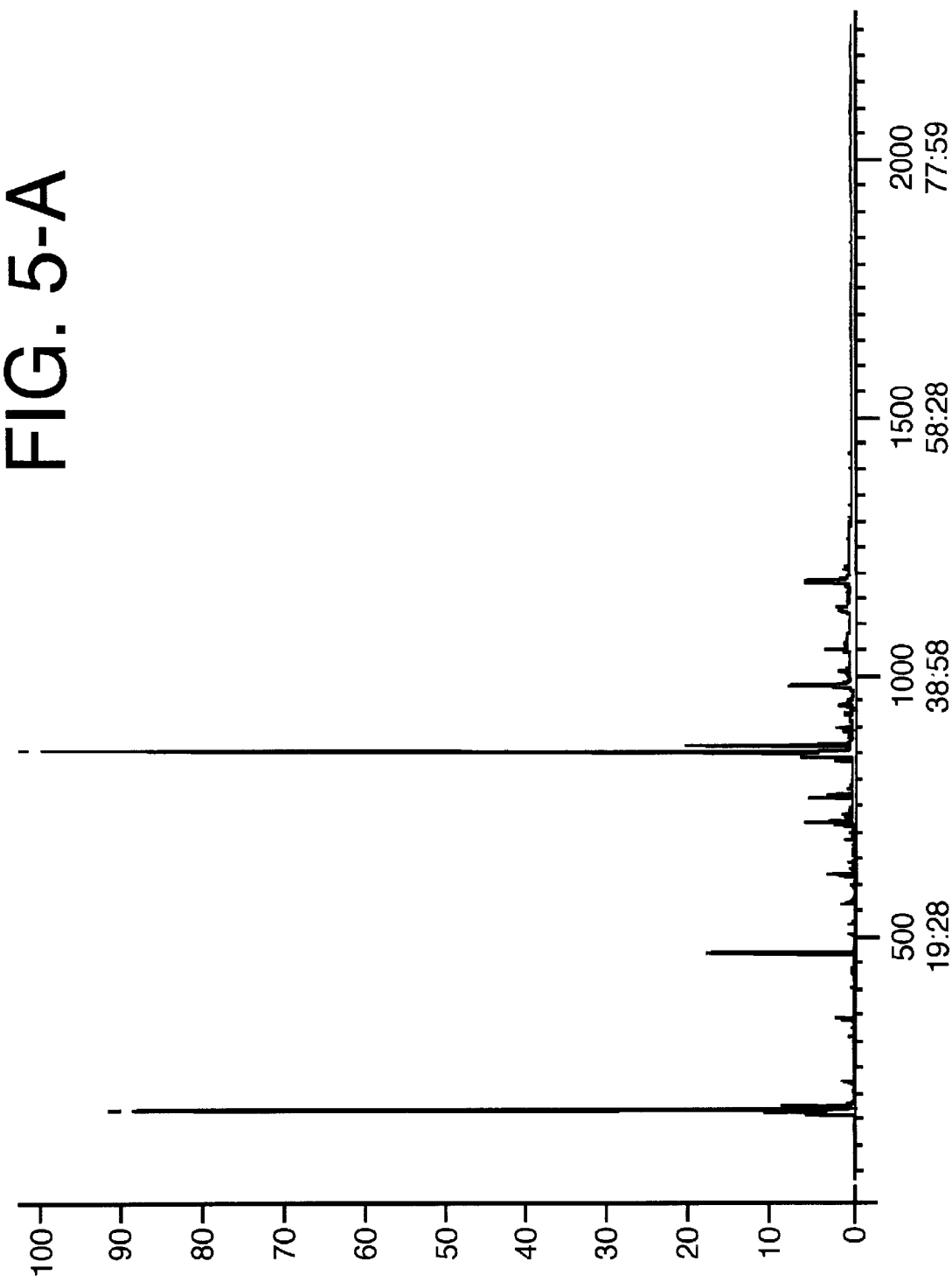

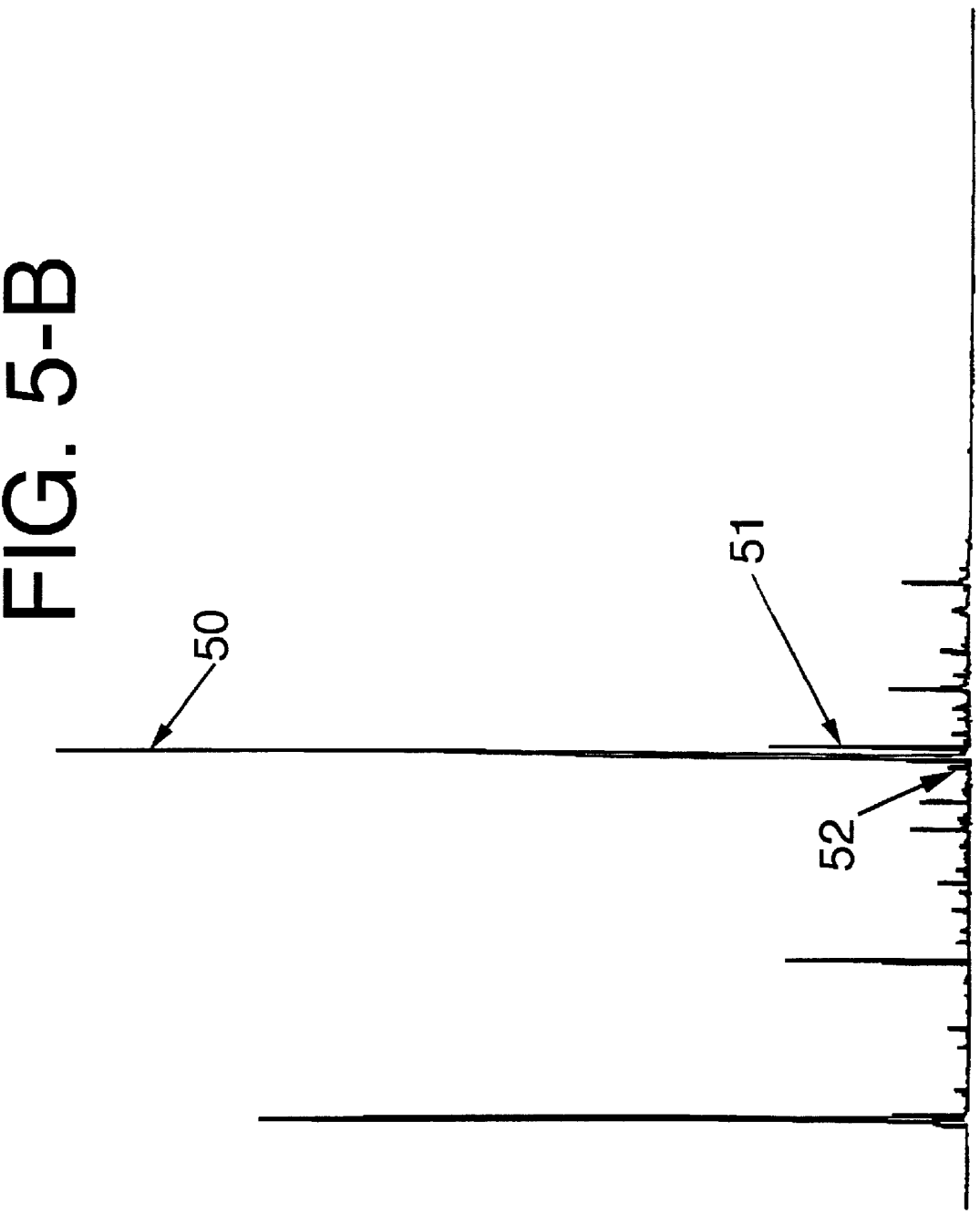

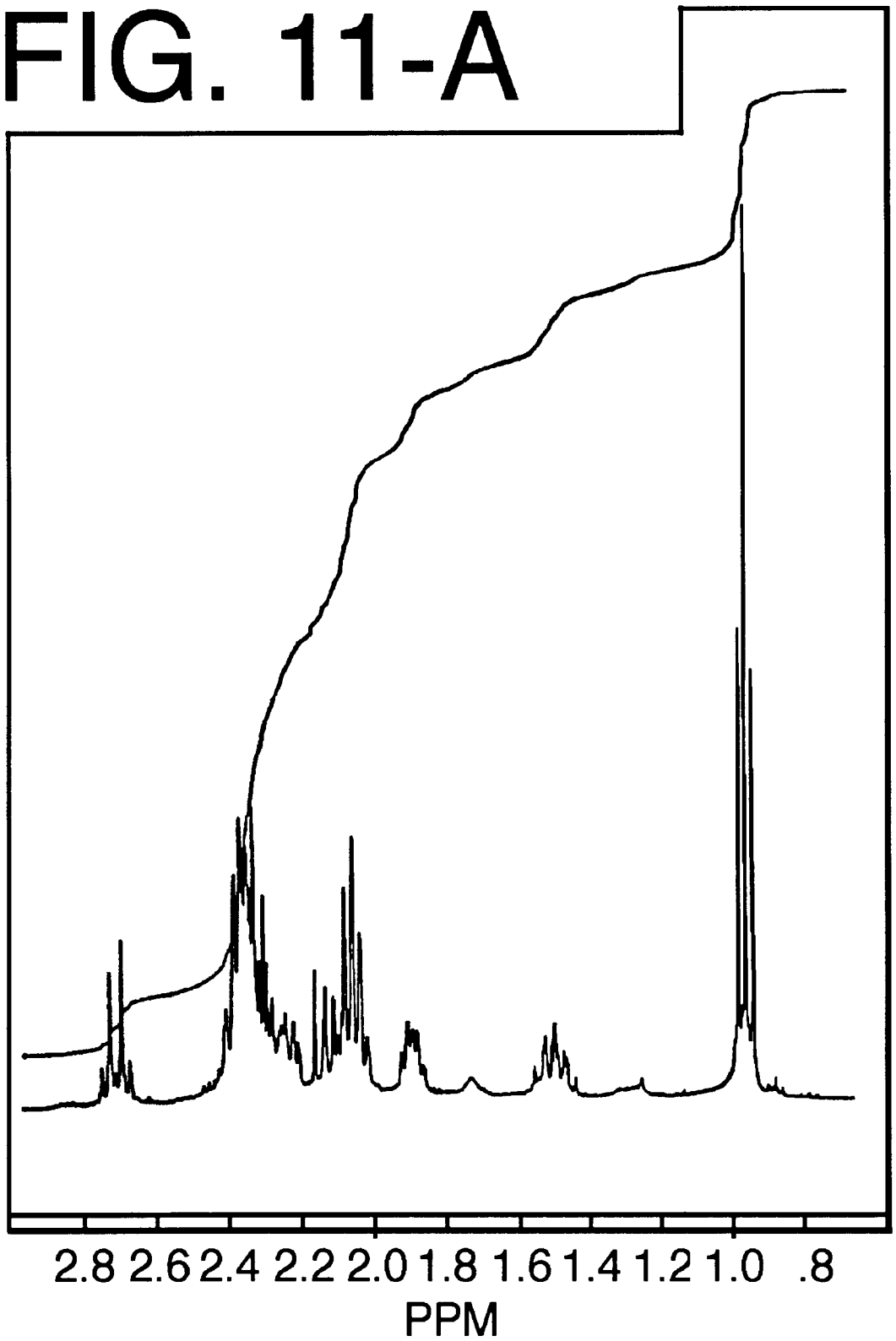
FIG. 11-A

FIG. 11-C
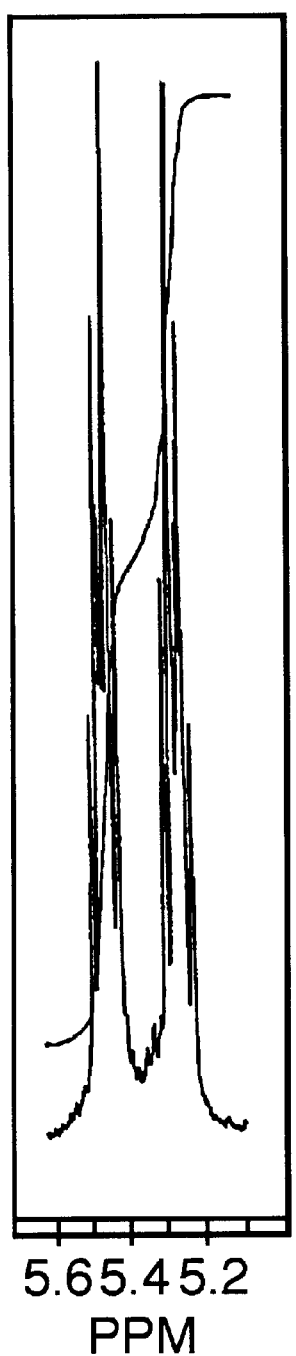
5.6 5.4 5.2
PPM
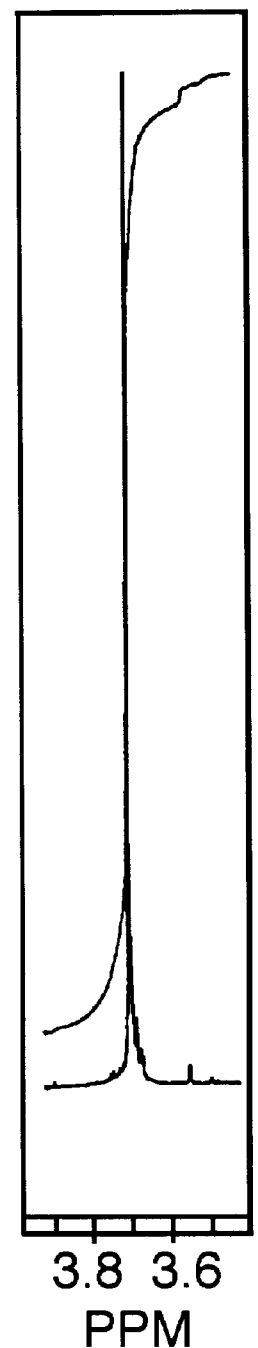
3.8 3.6
PPM
FIG. 11-B

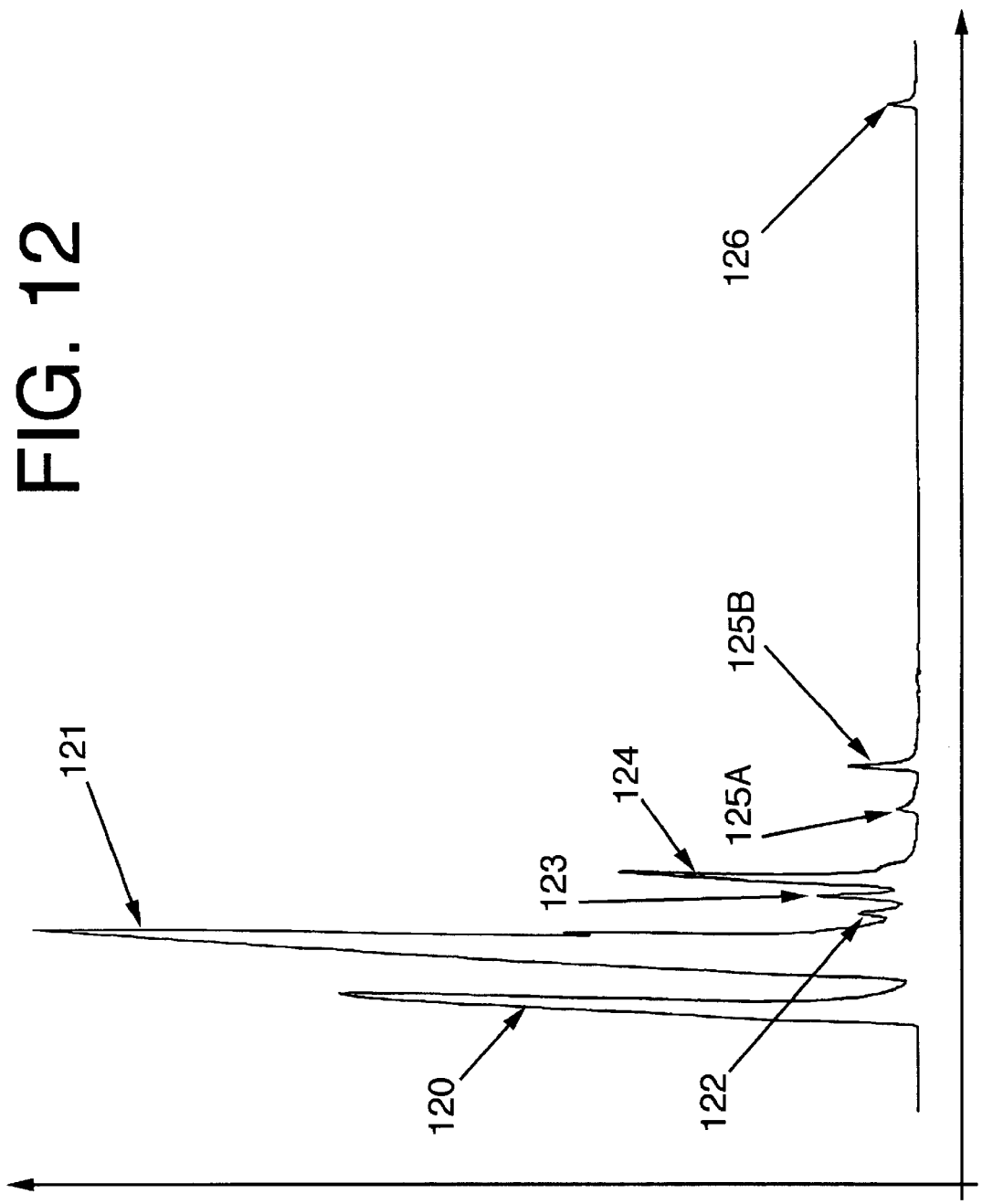

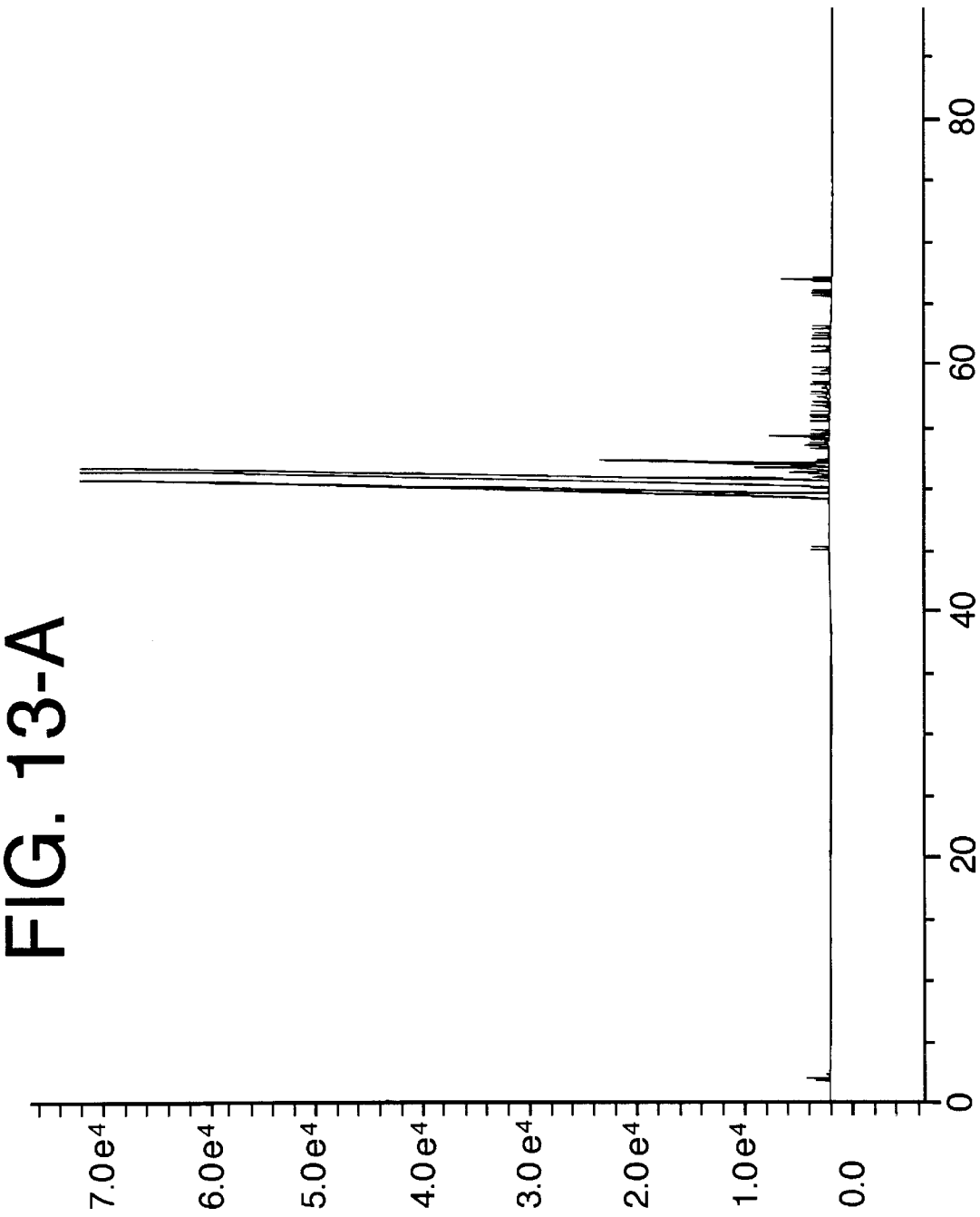
FIG. 13-A

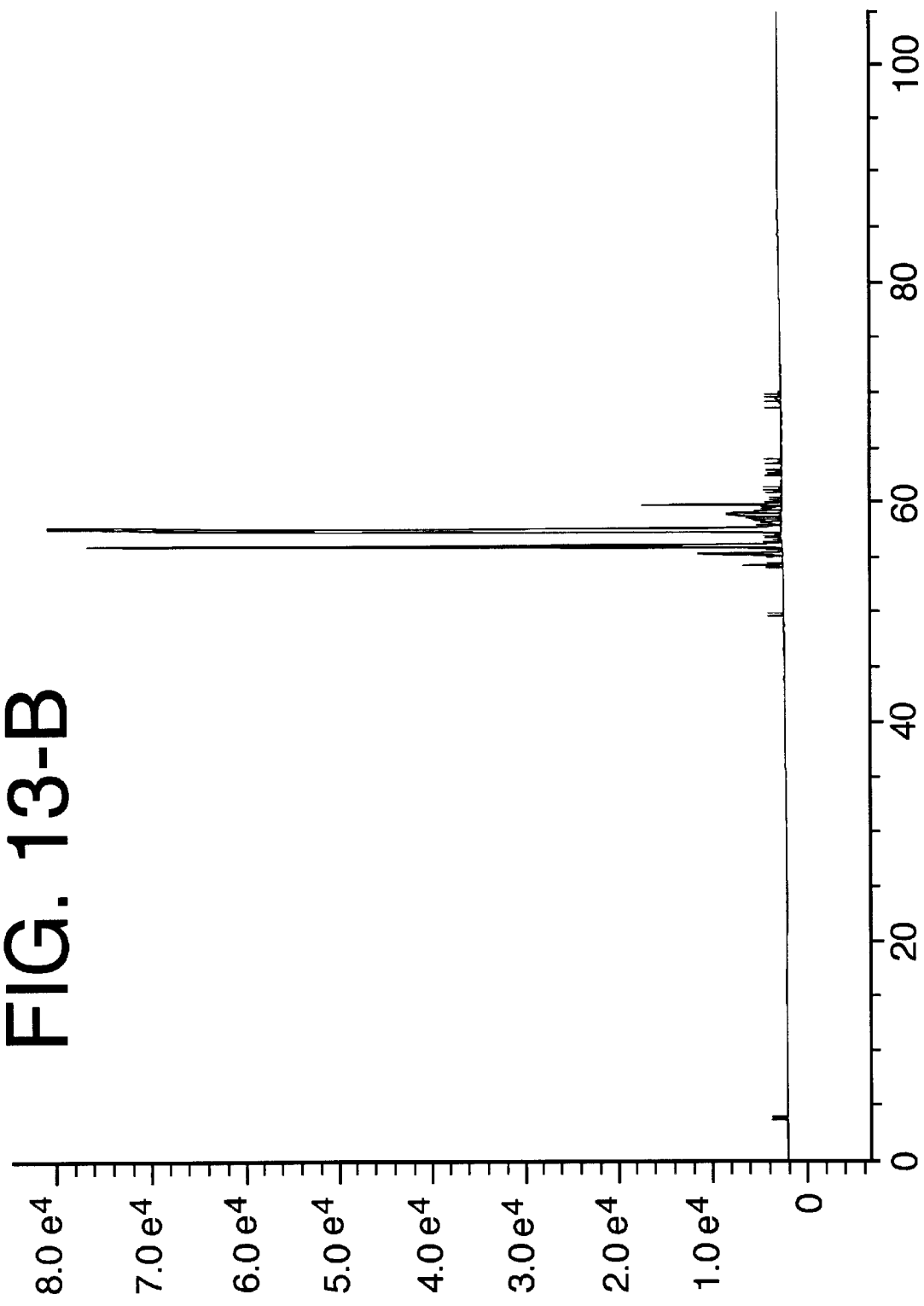
FIG. 13-B

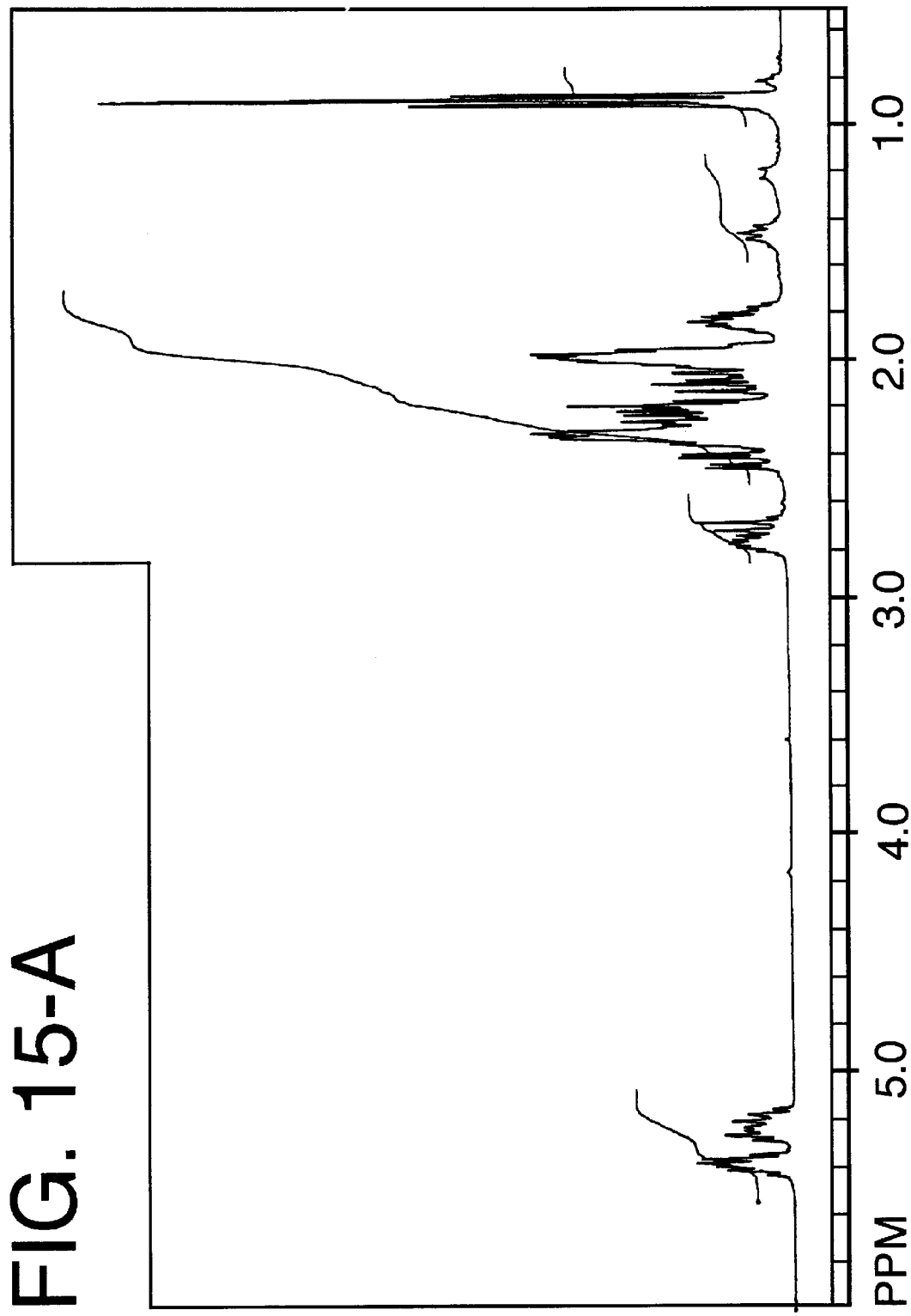
FIG. 15-A

US 6,333,180 B1

BIOPROCESS FOR THE HIGH-YIELD PRODUCTION OF FOOD FLAVOR-ACCEPTABLE JASMONIC ACID AND METHYL JASMONATE

BACKGROUND OF THE INVENTION

This invention concerns a microbial process for production of compositions of matter containing isomers of jasmonic acid having the structure:

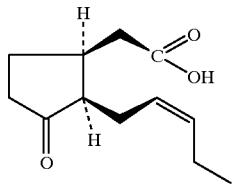

which are flavor acceptable as well as isomers having the structure:

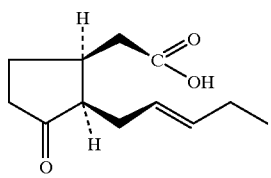

which are also flavor acceptable. This invention is also concerned with the production of methyl jasmonate isomers from the aforementioned jasmonic acid isomers.

Considerable time and effort have been expended by microbiologists in the search for better processes for the production of jasmonic acid and methyl jasmonate which are flavor acceptable isomers, including those isomers defined according to the structure:

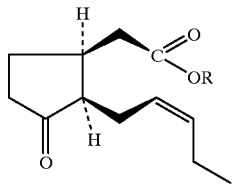

wherein R is methyl or hydrogen. Thus, Broadbent in United Kingdom Patent Specification No. 1,286,266 published on Aug. 23, 1972 discloses and claims a process for the manufacture of jasmonic acid which comprises cultivation of the organism *Lasiodiplodia theobromae* in a nutrient medium containing an assimilable source of carbon and an assimilable source of nitrogen followed by isolation of the product from the culture medium. Günther, et al, German Democratic Republic Patent DD 279 688 published on Jun. 13, 1990 discloses a process for the production of 7-iso-jasmonic acid by strains of the organism *Botryodiplodia theobromae* in aerobic culture. This work is also discussed in the paper Miersch, et al, *Phytochemistry*, Volume 26, No. 4, pages 1037–1039, 1987, entitled "(+)-7-ISO-JASMONIC ACID AND RELATED COMPOUNDS FROM BOTRYODIPLODIA THEOBROAME." The organisms, *Botryodiplodia theobromae* and *Lasiodermea theobromae* are synonyms of *Diplodia gossypina* as discussed in the paper Jones, MYCOTAXON, Volume VI, No. 1 at pages 24–26, July–September 1997 (title: "THE CURRENT TAXONOMIC STATUS OF DIPLODIA GOSSYPINA." As confirmed by Häusler and Münch in the article entitled "Microbial Production of Natural Flavors," Volume 63, No. 10, ASM News at pages 551–559:

"Another plant fatty acid metabolite, jasmonic acid, an endogenous plant growth regulator with a variety of physiological functions, is produced by means of a similar metabolic pathway. After a lipoxygenase produces a hydroperoxide derivative of linolenic acid, this compound is converted to its allene oxide, which cyclizes. β-Oxidation and double-bond reduction yields jasmonic acid. The methylester of jasmonic acid is not only a volatile plant hormone, possibly involved in interplant communication, but is also an important flavor and fragrance molecule that imparts a sweet-floral, jasmine-like note . . .

Otto Miersch and his collaborators at the Institute of Plant Biochemistry, Halle-Saale, Germany, who were studying fungal plant pathogens, including *Botryodiplodia theobromae*, discovered that such microorganisms produce jasmonic acid. The biosynthetic steps leading to jasmonic acid in this filamentous fungus are probably similar to those found in plants. Recently our laboratory, which is evaluating this strain's capacity for producing jasmonic acid, found that *B. theobromae* yields only very low concentrations of jasmonic acid in liquid culture. Such findings suggest that the biosynthesis and excretion of jasmonic acid is strictly controlled during the growth cycle of this fungus on plants in its natural habitat."no bioprocesses for the high yield production of fruit flavor-acceptable jasmonic acid or methyl jasmonate exist. The Häusler and Münch paper was published in October 1997. *ASM News* is published by the American Society for Microbiology.

Thus, in the flavor and fragrance art, a need has arisen for the development and efficient high yield production of naturally occurring jasmonic acid and methyl jasmonate, which have heretofore been found to be useful and necessary for the creation of flavor formulations used in augmenting or enhancing the aroma or taste of foodstuffs, chewing gums, toothpaste, medicinal products, chewing tobaccos and smoking tobaccos and also useful in augmenting or enhancing the aroma of perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like).

Methyl jasmonate (without indicating which isomer) is disclosed by Arctander, *Perfume and Flavor Chemicals* at monograph 2093 to have a "Powerful floral-herbaceous, sweet-tenacious odor representing typical background notes of Jasmin absolute." Arctander further discloses that this material "is an almost obvious candidate for work on improved artificial Jasmin absolute." Acree, et al, *J. Agric. Food Chem.*, 1985, Volume 33, pages 425–427, discloses that the isomer of methyl jasmonate having the structure:

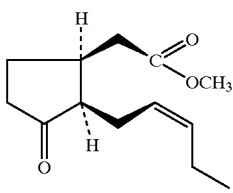

and having an optical rotation ($\alpha_D^{20}$) of +58 has a strong odor, whereas the other stereoisomers of (Z)-methyl jasmonate are substantially odorless.

No specific disclosures exist in the prior art showing the use of the jasmonic acid isomers of our invention defined according to the structure:

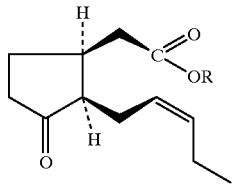

or defined according to the structure:

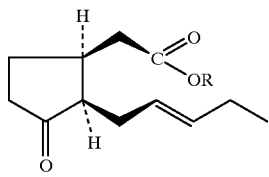

for use as flavor adjuvants (wherein R is methyl or hydrogen). Furthermore, nothing in the prior art discloses the stereoisomer of the compound having the structure:

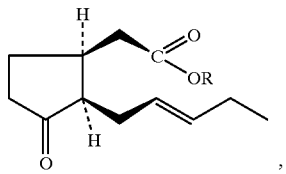

, particularly the stereoisomer having the optical rotation ($\alpha_D^{20}$) of +58°.

THE INVENTION

Our invention relates to a bioprocess for the high yield production of food flavor acceptable jasmonic acid and methyl jasmonate, a novel jasmonic acid isomer produced thereby and uses thereof. The process of our invention yields at least 5% of the "cis" isomer defined according to the structure:

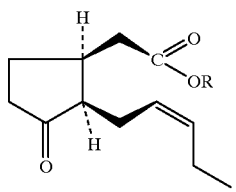

(wherein R is hydrogen or methyl) or the "cis" isomer defined according to the structure:

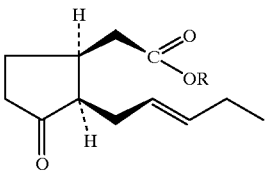

(wherein R is hydrogen or methyl). Compositions containing at least 98% of the isomer having the structure:

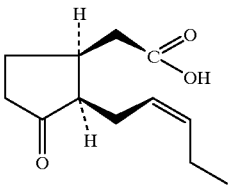

having an $\alpha_D^{20}$ of +58° are novel. Furthermore, compounds having the structure:

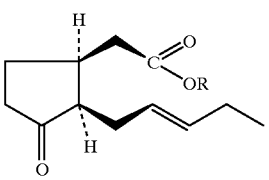

wherein R is methyl or hydrogen having an $\alpha_D^{20}$ of +58° are also novel.

The process of our invention comprises the cultivation under aerobic conditions of one or more specific strains of *Diplodia gossypina* in a nutrient medium followed by either (1) isolation of the jasmonic acid or (2) esterification of the jasmonic acid to form methyl jasmonate followed by isolation of the methyl jasmonate. More specifically, our process comprises cultivation under aerobic conditions of a strain of *Diplodia gossypina* organism selected from the group consisting of:

(i) *Diplodia gossypina* ATCC 10936;
(ii) *Diplodia gossypina* ATCC 20575;
(iii) *Diplodia gossypina* NRRL 25011; and
(iv) *Diplodia gossypina* ATCC 36037 in a nutrient medium containing an assimilable source of carbon and an assimilable source of nitrogen followed by isolation of the jasmonic acid product from the culture medium or followed by esterification of the jasmonic acid to form methyl jasmonate and then followed by isolation of the methyl jasmonate product from the reaction mass.

In one embodiment of the process of our invention, the compound, 10-oxo-trans-8-decenoic acid having the structure:

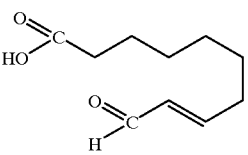

is intimately admixed in the nutrient medium in an amount of from about 0.7 up to about 10 ppm (parts per million) by weight of the nutrient medium prior to the cultivation step.

The 10-oxo-trans-8-decenoic acid having the structure:

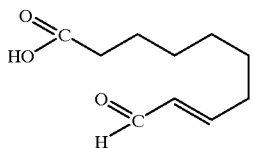

is disclosed in U.S. Pat. No. 5,681,738 issued on Oct. 28, 1997 to be a fungal growth hormone to stimulate mycelial growth of cultivated mushrooms. The specification of U.S. Pat. No. 5,681,738 issued on Oct. 28, 1997 is incorporated by reference herein. The bioprocess of our invention is shown according to the reactions:

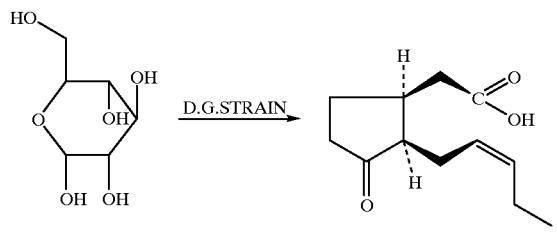

and

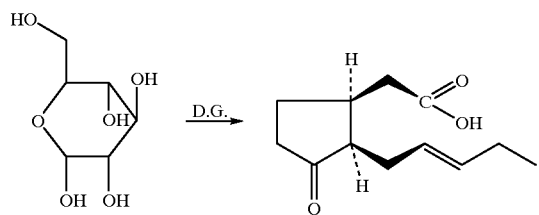

wherein D.G. strain is intended to mean "strain of *Diplodia gossypina.*"

The esterification reaction following the bioprocess reaction of our invention is shown as follows:

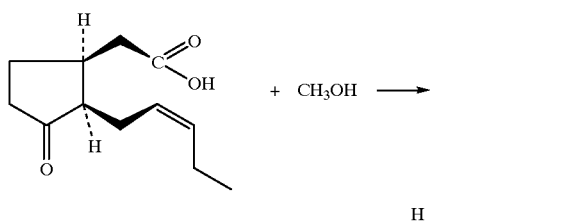

and

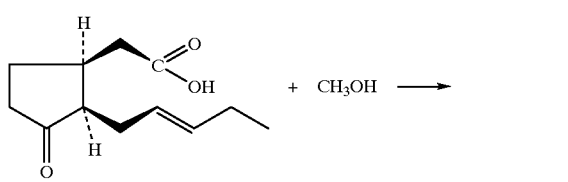

-continued

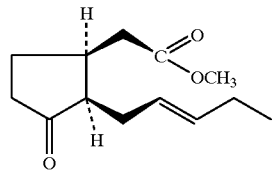

Thus, the assimilable carbon source for our invention has been found to be gl prepared according to the reactions:
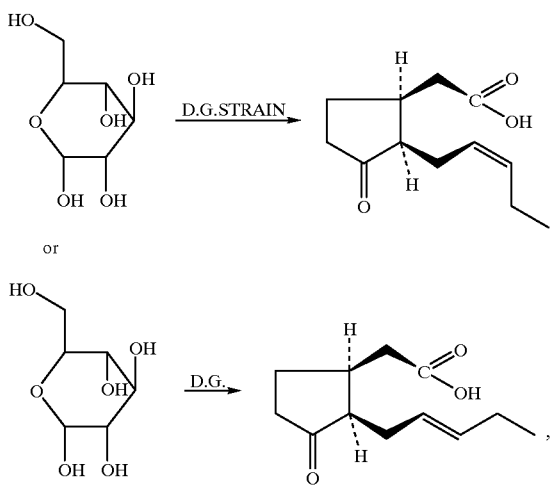

or

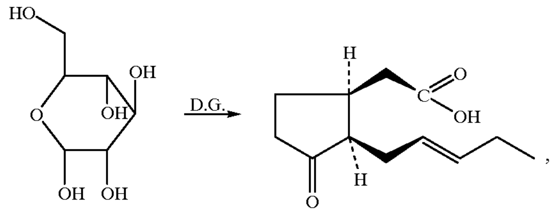

, other jasmonic acid isomers defined according to the structures:

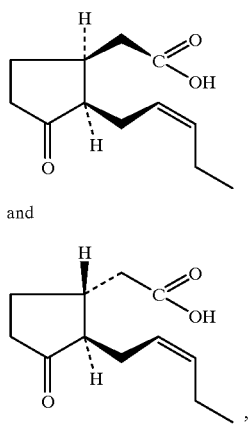

and

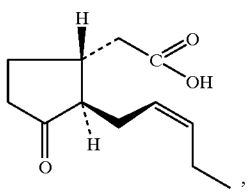

, for example, are also produced in very small quantities when using the strains of *Diplodia gossypina:*

(i) *Diplodia gossypina* ATCC 10936;

(ii) *Diplodia gossypina* ATCC 20575;

(iii) *Diplodia gossypina* NRRL 25011; and (iv) *Diplodia gossypina* ATCC 36037.

The inventive process may be conducted in a batch or continuous mode of operation. In a batch fermentation, the nutrient broth, culture and substrate, are combined and fermented until the jasmonic acid concentration becomes constant. In a continuous process, the substrate in the nutrient broth may be continuously recirculated through a fermentation reactor, with the provision that substrate and product are respectively added and removed from the recirculating broth.

In carrying out the present invention, cultivation and fermentive incubation of the *Diplodia gossypina* fungus are accomplished in an aqueous medium in the presence of the usual nutrient substances (preferably using sodium nitrate, magnesium sulfate heptahydrate and glucose). A suitable medium thus is one which contains carbon sources, nitrogen sources, inorganic salts and growth factors. Additional examples of inorganic salts include the phosphate salts of magnesium and the phosphate and sulfate salts of sodium, calcium and potassium. These nutrients may be supplemented with, for example, one or more vitamins of the "B" group and one or more trace minerals such as iron, manganese, cobalt and copper, as desired.

For the nutrient broth, it is preferred to utilize glucose (as stated, supra) at a concentration of from about 2 up to about 20 weight percent, preferably at about 10 weight percent. It is also preferred to employ "B" vitamins either as a separate supplement or in the form of a yeast extract. The kind and amounts of these additives can be determined by applying the general knowledge in the art for the cultivation of microorganisms.

In a typical procedure, one of the *Diplodia gossypina* organisms:

(i) *Diplodia gossypina* ATCC 10936;

(ii) *Diplodia gossypina* ATCC 20575;

(iii) *Diplodia gossypina* NRRL 25011; or (iv) *Diplodia gossypina* ATCC 36037 is first cultivated in inoculum quantities to produce a mature culture in nutrient broth. The culture is inoculated into a fermentor nutrient broth and allowed to establish itself. The substrate is then added and fermentation is continued until a steady concentration of jasmonic acid is present.

The cultivation and fermentative incubation of the *Diplodia gossypina* fungus can be carried out as a stationary culture or as a submerged culture (e.g., shake-flask fermentor) under aerobic conditions. Cultivation and incubation may proceed as stated, supra, in a pH range of from about 4.5 up to about 9, preferably at 6. The pH may be regulated by the addition of an inorganic or organic acid or base such as hydrochloric acid, acetic acid, sodium hydroxide, calcium carbonate, ammonia, ion-exchange resins or by the addition of a buffer such as phosphate or phthalate. The incubation temperature as stated, supra, is suitably maintained between about 20° C. up to about 35° C., with a range of from about 25° C. up to about 32° C. being preferred.

In accordance with another typical procedure of the present invention, the process is conveniently carried out by adding the substrate to the culture medium at the onset of cultivation under aerobic conditions. Alternatively, the substrate may be added either alone or in combination with another carbon source, such as xylose during fermentative incubation or when cultivation is complete. It is preferable to add the substrate to the culture medium during the period of from 4 up to 24 hours after the growth of the culture in the fermentative broth has commenced. Desirable results can be obtained when the substrate is added continuously over the entire fermentation after an initial fungal (*Diplodia gossypina*) cultivation period of from 3 up to 12 hours. A preferred feed rate for this continuous addition is from about 0.01 up to 1 gram per hour per liter, with a preferred range of from 0.6 up to 0.8 grams per hour per liter. The concentration of the substrate in the medium may vary depending on the conditions employed. In practice, the concentration of the substrate in the medium may conveniently vary from 0.01% up to about 10%, with a preferable concentration of about 1% by weight consistent with the manner in which it is added to the culture.

The present invention provides unexpectedly high yields of jasmonic acid, e.g., from about 0.8 up to about 1.5 grams per liter.

Another aspect of our invention is the production of methyl jasmonate isomers having the structure:

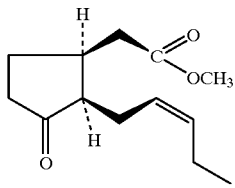

and having the structure:

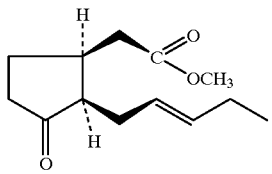

In this case, the isolation step comprises the steps of:
(a) extraction of the jasmonic acid from the fermentation broth with an extraction solvent such as ethyl acetate to form ajasmonic acid extract;
(b) concentration of the jasmonic acid extract whereby the extraction solvent is stripped;
(c) esterification of the resulting jasmonic acid with methyl alcohol whereby the methyl jasmonate is formed according to one of the reactions:

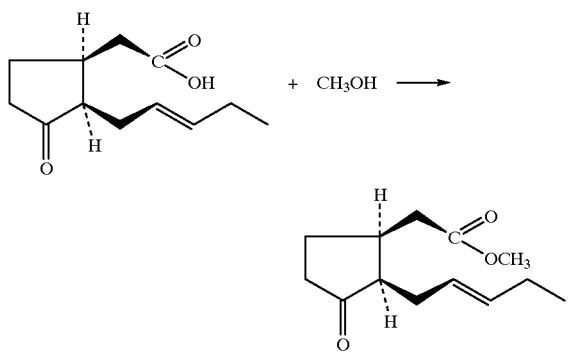

or:

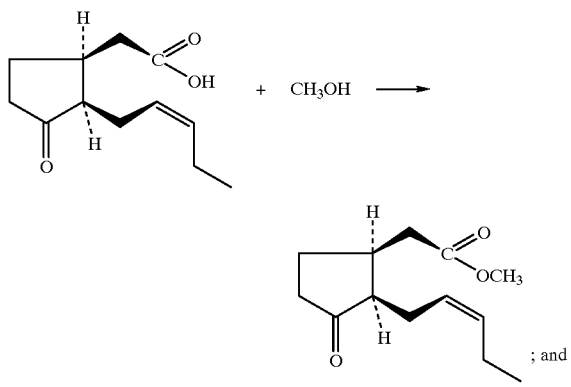

; and (d) concentration of the resulting methyl jasmonate.

Additional steps of fractionation of the resulting concentrate with, for example, silica gel, in order to effect isomer separation and then collecting the 98% "cis" isomer are preferred.

Thejasmonic acid derivative(s) defined according to the structure:

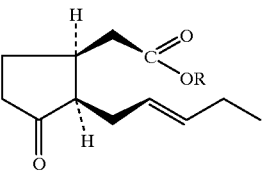

or according to the structure:

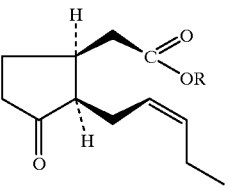

(wherein R is methyl or hydrogen) and one or more auxiliary perfume ingredients including, for example, hydrocarbons, alcohols, ketones (other than the jasmonic acid derivatives of our invention), aldehydes, nitrites, esters (other than the jasmonic acid derivatives of our invention), ethers, synthetic essential oils and natural essential oils, may be admixed so that the combined odors of the individual components produce a pleasant and desired fragrance, particularly and preferably in the floral area (e.g., jasmine and jasmine/rose aromas). Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, it is the individual components which contribute to their particular olfactory characteristics; however, the overall sensory effect of the perfume composition will be at least the sum total of the effects of each of the ingredients. Thus, one or more of the jasmonic acid derivative(s) of our invention can be used to alter, modify or enhance the aroma characteristics of a perfume composition, for example, by utilizing or moderating the olfactory reaction contributed by another ingredient in the composition. Thus, a suitable mixture would be that of the cis isomers of jasmonic acid and methyl jasmonate, to wit: the mixture of the compounds having the structures:

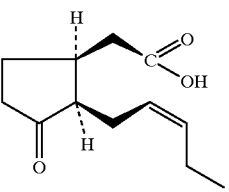

and

-continued

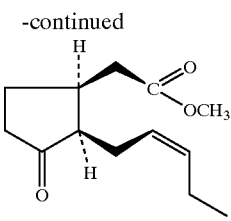

or the mixture of compounds having the structures:

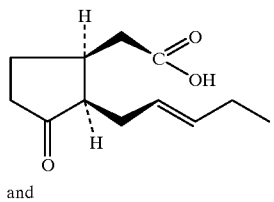

and

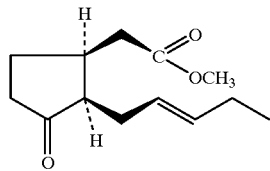

The amount of jasmonic acid derivative(s) of our invention, which will be effective in perfume compositions as well as in perfumed articles and colognes, depends upon many factors including the other ingredients, their amounts and the side effects which are desired. It has been found that perfume compositions containing as little as 0.005% of the jasmonic acid derivative(s) or even less (e.g., 0.002%) can be used to impart powerfuL long lasting jasmine, floral-herbaceous aromas with sweet-herbaceous, green-woody topnotes to soaps, cosmetics, detergents including anionic, cationic, nonionic and zwitterionic solid or liquid detergents, perfumed polymers and other products. The amounts employed can range up to 70% of the fragrance components and will depend upon considerations of cost, nature of the end product, the effect desired on the finished product and the particular fragrance sought.

The jasmonic acid derivative(s) of our invention are useful (taken alone or taken together with other ingredients in perfume compositions) in detergents, soaps, space odorants and deodorants, perfumes, colognes, toilet waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the jasmonic acid derivative(s) will suffice to impart an intense and long lasting jasmine, floral-herbaceous aroma with sweet-herbaceous, green-woody topnotes to floral perfume formulations. Generally no more than 5% of the jasmonic acid derivative(s) based on the ultimate end product are required to be used in the perfume compositions.

Furthermore, as little as 0.25% of the jasmonic acid derivative(s) will suffice to impart such aromas to perfumed articles per se, whether in the presence of other perfume materials or whether used by themselves. Thus, the range of use of the jasmonic acid derivative(s) of our invention in perfumed articles, e.g., perfumed polymers and solid or liquid anionic, cationic, nonionic or zwitterionic solid or liquid detergents, may vary from 0.25% up to about 5% by weight based on the total weight of the perfiuned article.

In addition, the perfume composition or fragrance composition of our invention can contain a vehicle or carrier for the jasmonic acid derivative(s). The vehicle can be a liquid such as a nontoxic alcohol, e.g., ethanol; a nontoxic glycol e.g., propylene glycol; or the like. The carrier can also be an absorbent solid such as a gum (e.g., gum arabic, xanthan gum or guar gum) or components for encapsulating the composition by means of coacervation (such as gelatin) or by means of formation of a polymer around a liquid center (as by using a urea formaldehyde prepolymer to form a polymeric capsule around a perfume composition center).

It will be appreciated from the present disclosure that the jasmonic acid derivative(s) according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify its organoletpic character.

The term "enhance" is intended herein to mean the intensification (by use of the jasmonic acid derivative of our invention) of a flavor or aroma note or nuance in a tobacco flavor or foodstuff or perfume composition or perfumed article without changing the quality of said note or nuance.

A "flavoring composition" is taken to mean one which contributes a part of the overall flavor impression by supplementing or forfing a natural or artificial flavor in a material, or one which supplies substantially all the flavor and/or aroma character to a consumable article.

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat foods, other veterinary products and the like. The jasmonic acid derivative(s) of our invention are also useful in tobacco flavorants and tobacco enhancers.

The term "tobacco" will be understood herein to mean natural products such as, for example, Burley, Turkish tobacco, Maryland tobacco, flue-cured tobacco and the like, including tobacco-like or tobacco-based products such as reconstituted or homogenized leaf and the like, as well as tobacco substitutes intended to replace natural tobacco such as lettuce and cabbage leaves and the like. The tobaccos and tobacco products in which the jasmonic acid derivative(s) of our invention are useful include those designed or used for smoking such as in cigarettes, cigar and pipe tobacco, as well as products such as snuff, chewing tobacco and the like.

When the jasmonic acid derivative(s) of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the jasmonic acid derivative (s) of our invention; (2) that they be organoleptically compatible with the jasmonic acid derivative(s) of our invention whereby the flavor of the ultimate consumable material to which the jasmonic acid derivative(s) are added is not detrimentally affected by the use of the adjuvant; and (3) that they be ingestibly acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones (other than the jasmonic acid derivatives of our invention) and aldehydes; lactones; other cyclic organic materials including benzene derivatives, alicyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as cocoa, vanilla and caramel; essential oils and extracts such as anise oil, clove oil and the like and artificial flavoring materials such as vanillin, ethyl vanillin and the like.

Specific preferred flavor adjuvants are as follows:

anise oil;
ethyl-2-methyl butyrate;
vanillin;
cis-3-heptenol;
cis-3-hexenol;
trans-2-heptenal;
butyl valerate;
2,3-diethyl pyrazine;
methyl cyclopentenolone;
benzaldehyde;
valerian oil;
3,4-dimethoxyphenol;
amyl acetate;
amyl cinnamate;
γ-butyryl lactone;
furfural;
trimethyl pyrazine;
phenyl acetic acid;
isovaleraldehyde;
ethyl maltol;
ethyl vanilin;
ethyl valerate;
ethyl butyrate;
cocoa extract;
coffee extract;
peppermint oil;
spearmint oil;
clove oil;
anethol;
cardamom oil;
wintergreen oil;
cinnamic aldehyde;
ethyl-2-methyl valerate;
γ-hexenyl lactone;
2,4-decadienal;
2,4-heptadienal;
methyl thiazole alcohol (4-methyl-5-β-hydroxyehtyl thiazole);
2-methyl butanethiol;
4-mercapto-2-butanone;
3-mercapto-2-pentanone;
1-mercapto-2-propane;
benzaldehyde;
furfural;
furfuryl alcohol;
2-mercapto propionic acid;
alkyl pyrazine;
methyl pyrazine;
2-ethyl-3-methyl pyrazine;
tetramethyl pyrazine;
polysulfides;
dipropyl disulfide;
methyl benzyl disulfide;
alkyl thiophene;
2,3-dimethyl thiophene;
5-methyl furfural;
acetyl furan;
2,4-decadienal;
guiacol;
phenyl acetaldehyde;
β-decalactone;
d-limonene;
acetoin;
amyl acetate;
maltol;
ethyl butyrate;
levulinic acid;
piperonal;
ethyl acetate;
n-octanal;
n-pentanal;
n-hexanal;
diacetyl;
monosodium gulatamate;
monopotassium glutamate;
sulfur-containing amino acids, e.g., cysteine;
hydrolyzed vegetable protein;
2-methylfuran-3-thiol;
2-methyldihydrofuran-3-thiol;
2,5-dimethylfuran-3-thiol;
2 hydrolyzed fish protein;
tetramethyl pyrazine;
propylpropenyl disulfide;
propylpropenyl trisulfide;
diallyl disulfide;
diallyl trisulfide;
dipropenyl disulfide;
dipropenyl trisulfide;
4-methyl-2-[(methylthio)-ethyl]-1,3-dithiolane;
4,5-dimetyl-2-(methylthiomethyl)-1,3-dithiolne; and
4-methyl-2-(methylthiomethyl)-1,3-dithiolane.

The jasmonic acid derivative(s) of our invention or compositions incorporating them, as mentioned above, can be combined with one or more vehicles or carriers for adding them to the particular product. Vehicles can be edible or otherwise suitable materials such as ethyl alcohol propylene glycol, water and the like, as described supra. Carriers include materials such as gum arabic, carrageenan, xanthan gum, guar gum and the like.

The jasmonic acid derivative(s) prepared according to our invention can be incorporated with the carriers by conventional means such as spray-drying, drum-drying and the like. Such carriers can also include materials for coacervating the jasmonic acid derivative(s) of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of jasmonic acid derivative(s) utilized should be sufficient to impart the desired flavor characteristic to the product, but on the other hand, the use of an excessive amount of the jasmonic acid derivative(s) is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.1 parts per million (ppm) up to about 500 ppm of the jasmonic acid derivative(s).

The jasmonic acid derivative(s) of our invention when utilized in flavoring compositions can be varied over a wide range depending upon the particular flavor nuances desired to be added to the foodstuff. Thus, the amounts of jasmonic acid derivative(s) of our invention may be contained in flavoring materials from about 1 ppm up to about 50% by weight of the flavoring composition. Indeed, the compounds having the structures:

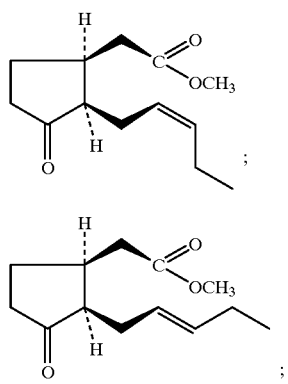

-continued

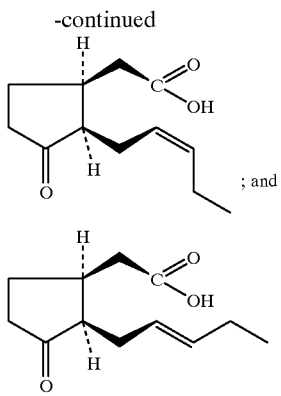

may be utilized in raspberry flavors (e.g., for use in raspberry-flavored yogurt, for example) at levels of between about 1% and about 50%. Such materials also have utility in flavorings for salad dressings, particularly in such cuisines as "Thai" cuisine.

According to another aspect of our invention, an organoleptically improved smoking tobacco product and additives therefor as well as methods of making the same which overcome specific problems heretofore encountered in which specific Turkish, oriental-like aromas prior to smoking and improved Turkish, oriental aromas on smoking in the mainstream and the side stream are created or enhanced or modified or augmented and may be readily controlled and maintained at the desired uniform level regardless of variations in the tobacco components of the blend. In particular, low grade Virginia-type tobaccos may be upgraded using the jasmonic acid derivative(s) of our invention.

This invention further provides improved tobacco additives and methods whereby various desirable natural aromatic Turkish tobacco flavoring characteristics with oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more of the jasmonic acid derivative(s) of our invention.

In addition to the jasmonic acid derivative(s) of our invention, other flavoring and aroma additives may be added to the smoking tobacco material or substitute therefor, either separately or in admixture with the jasmonic acid derivative (s) of our invention as follows:

I. Synthetic Materials
    β-Ethyl-cinnamaldehyde;
    Eugenol;
    Dipentene;
    β-Damascenone;
    Maltol;
    Ethyl maltol;
    Delta-Undecalactone;
    Delta-Decalactone;
    Benzaldehyde;
    Amyl acetate;
    Ethyl butyrate;
    Ethyl valerate;
    Ethyl acetate;
    2-Hexenol-1;

2-Methyl-5-isopropyl-1,3-nonadiene-8-one;

2,6-Dimethyl-1,6-undecadiene-10-one;

2-ethyl-5-isopropyl acetophenone;

2-Hydroxy-2,5,5,8a-tetramethyl-1-(2-hydroxyethyl)-decahydronnaphthalene;

Dodcahydro-3a,6,6,9a-tetramethyl naphthol(2,1-b) furan;

4-Hydroxy hexanoic acid, γ-lactone; and

Polyisoprenoid hydrocarbons defined in Example V of U.S. Pat. No. 3,589,372 issued on Jun. 29, 1971.

II. Natural Oils

Celery seed oil;

Coffee extract;

Bergamot oil;

Cocoa extract;

Nutmeg oil; and

Origanum oil.

An aroma and flavoring concentrate containing one or more of the jasmonic acid derivative(s) of our invention and, if desired, one or more of the above-indicated additional flavoring additives may be added to the smoking tobacco material, to the filter or to the leaf or paper wrapper. The smoldng tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of oriental and/or Turkish tobacco notes, we have found that satisfactory results are obtained if the proportion by weight of the sum total of jasmonic acid derivative(s) to smoking tobacco material is between 50 ppm and 1,500 ppm (0.005%–0.15%) of the active ingredients to the smoking tobacco material. We have further found that satisfactory results are obtained if the proportion by weight of the sum total of jasmonic acid derivative(s) used to flavoring material is between 500 and 15,000 ppm (0.05%–1.5%).

Any convenient method for incorporating the jasmonic acid derivative(s) into the tobacco product may be employed. Thus, the jasmonic acid derivative(s) taken alone or along with other flavoring additives may be dissolved in a suitable solvent such as ethanol, diethyl ether and/or other organic solvents, and the resulting solution may either be spread onto the cured, cased and blended tobacco material or the tobacco material may be dipped into such solution. Under certain circumstances, a solution of the jasmonic acid derivative(s) taken alone or taken further together with flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have the jasmonic acid derivative(s) in excess of the amounts or concentrations above indicated so that when blended with other tobaccos, the final product will have the percentage within the indicated range.

In accordance with one specific example of our invention, an aged, cured and shredded domestic Virginia tobacco is sprayed with a 20% alcohol solution of the compound having the structure:

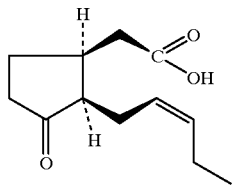

optical rotation ($\alpha_D^{20}$) equal +58° on a dry basis. Thereafter, the alcohol is removed by evaporation and the tobacco is manufactured into cigarettes by the usual techniques. The cigarette, when treated as indicated, has a desired and pleasing aroma which is detectable in the mainstream and the side stream when the cigarette is smoked. The aroma is described as being sweeter with pronounced Turkish/oriental characteristics and with improved body and enhanced tobacco character with subsidiary "floral," "jasmonic" nuances in the mainstream and the side stream. In addition, interesting amber nuances are imparted.

While our invention is particularly useful in the manufacture of smoking tobacco such as cigarette tobacco, cigar tobacco and pipe tobacco, other tobacco products formed from sheeted tobacco dust or fines may also be used. Likewise, the jasmonic acid derivative(s) of our invention can be incorporated with materials such as filter tip materials, seam paste, packaging materials and the like, which are used along with tobacco to form a product adapted for smoking. Furthermore, the jasmonic acid derivative(s) can be added to certain tobacco substitutes of natural or synthetic origin (e.g., dried lettuce leaves) and, accordingly, by the term "tobacco" as used throughout this specification, is meant any composition intended for human consumption by smoking or otherwise when composed of tobacco plant parts or substitute material or both. Thus, chewing tobacco is also included in the foregoing meaning of "tobacco."

During the fermentation reaction of our invention, two byproducts are also formed, to wit, the compound having the structure:

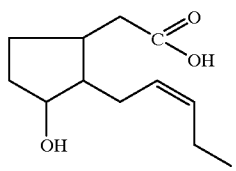

and the compound having the structure:

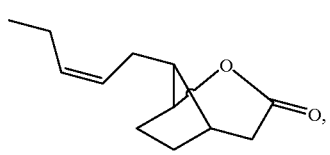

the compound having the structure:

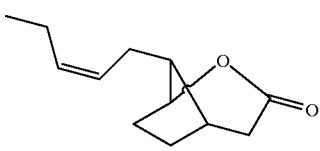

formed via the reaction:

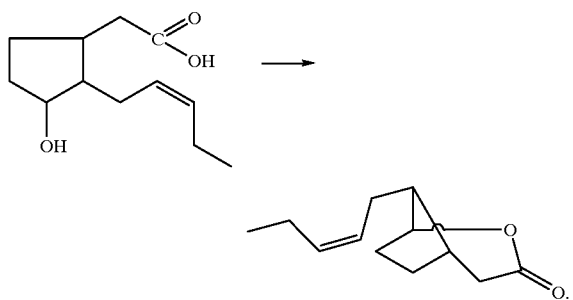

It will be understood that each of the compounds having the structures:

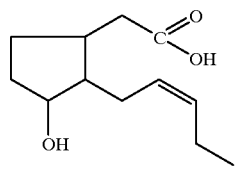

and

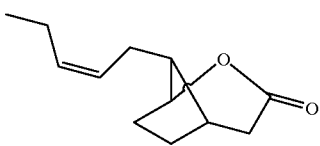

may be retained with the jasmonic acid derivative(s) of our composition for their flavor or fragrance utilities. Thus, in addition to the additives as set forth, supra, the compounds having the structures:

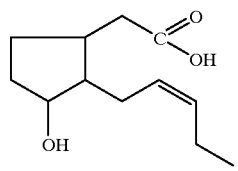

and

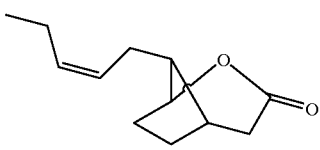

may be "retained" and not "separated" in the isolation of the jasmonic acid derivative(s) prior to the jasmonic acid derivative(s) being utilized in flavor or fragrance formulations.

More specifically, our invention also contemplates mixtures of derivatives having the structures:

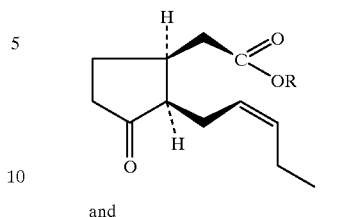

and

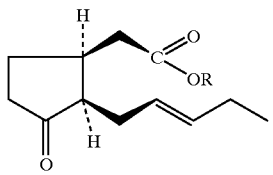

(wherein R is methyl or hydrogen) taken further together with the compounds having the structures:

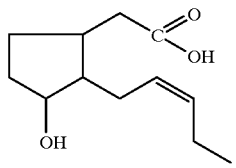

and/or

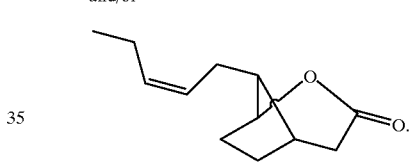

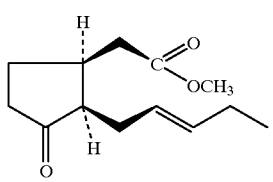

and

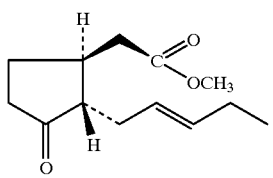

Figure 4:
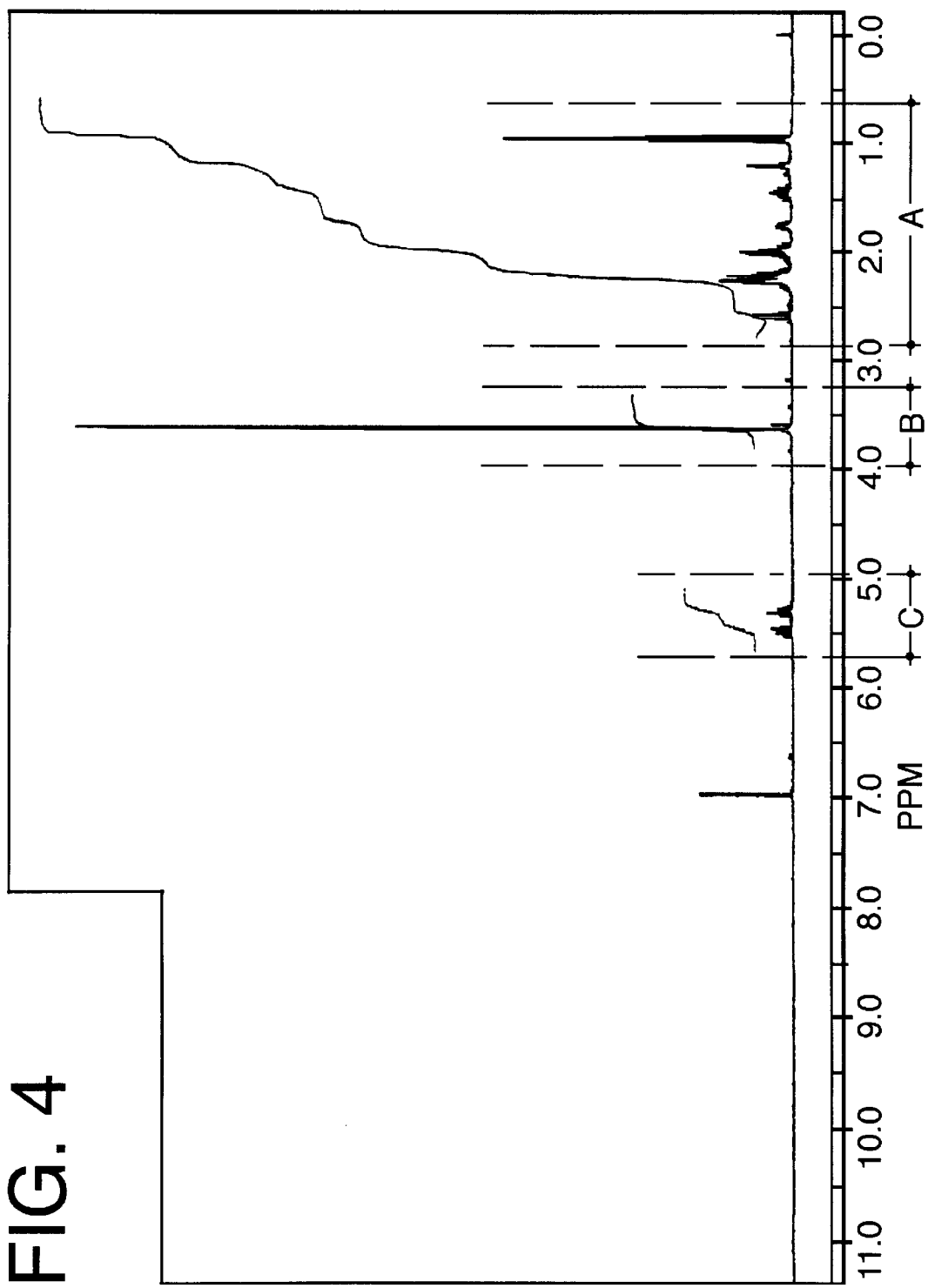

FIG. 4 is the NMR spectrum for the product of Example XV for the compound having the structure:

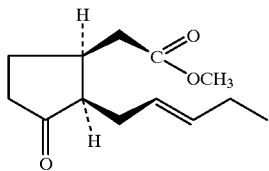

(optical rotation $(\alpha_D^{20})$=+58).

FIG. 4A is an enlargement of section "A" of the NMR spectrum of FIG. 4.

FIG. 4B is an enlargement of section "B" of the NMR spectrum of FIG. 4.

FIG. 4C is an enlargement of section "C" of the NMR spectrum of FIG. 4.

FIG. 5A is a GC mass spectrum for the compound having the structure:

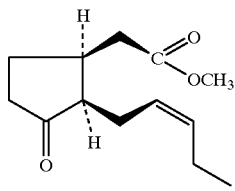

$(\alpha_D^{20}$=+58°) prepared according to Example XV.

FIG. 5B is the GC mass spectrum for the product produced according to Example XV having the structure:

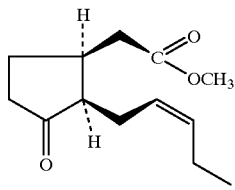

together with small amounts of the compound defined according to the structure:

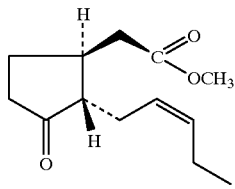

with the optical rotation for the compound having the structure:

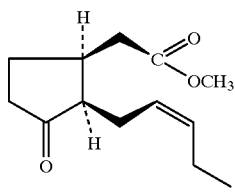

being $(\alpha_D^{20})$+58°.

Figure 6:
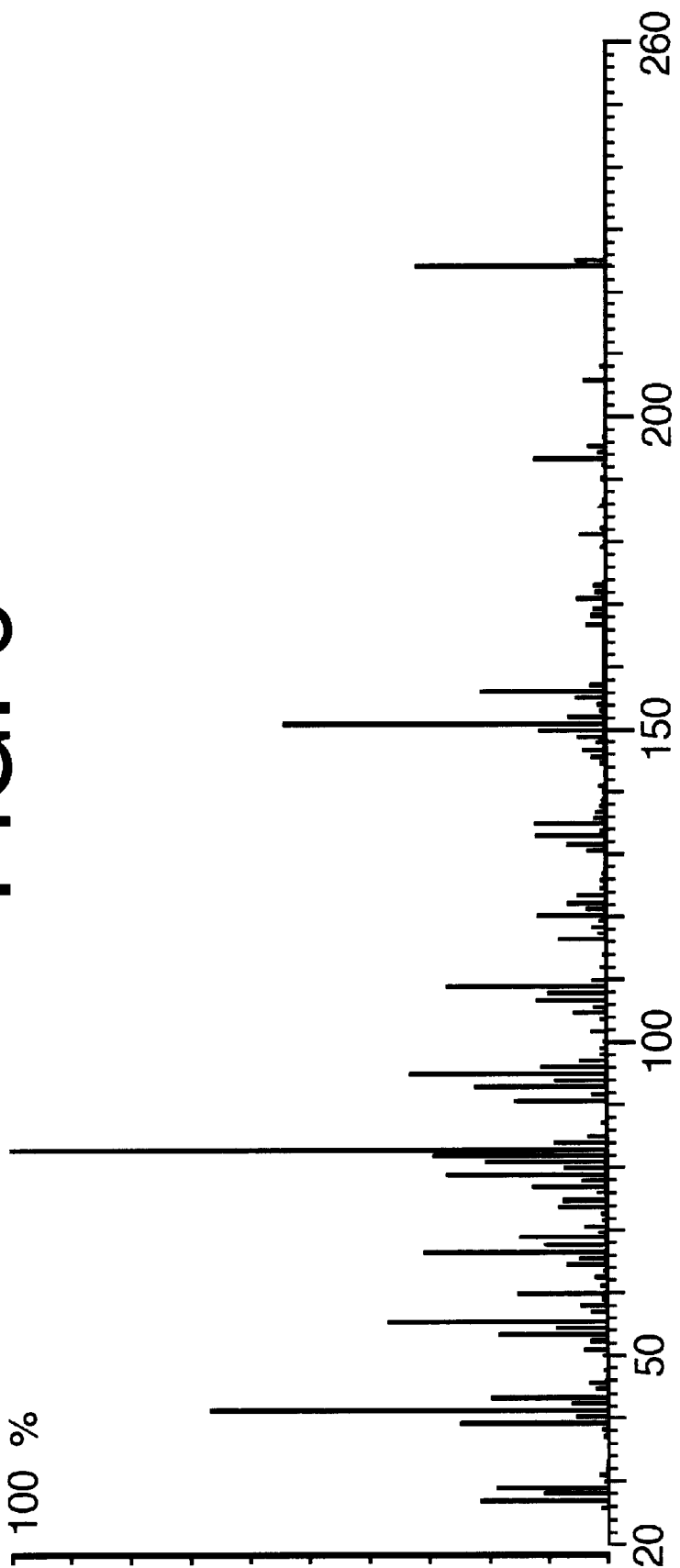

FIG. 6 is the mass spectrum for the compound having the structure:

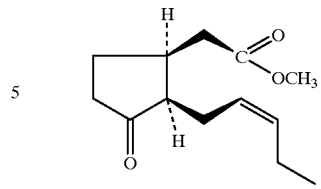

prepared according to Example XV.

Figure 7:
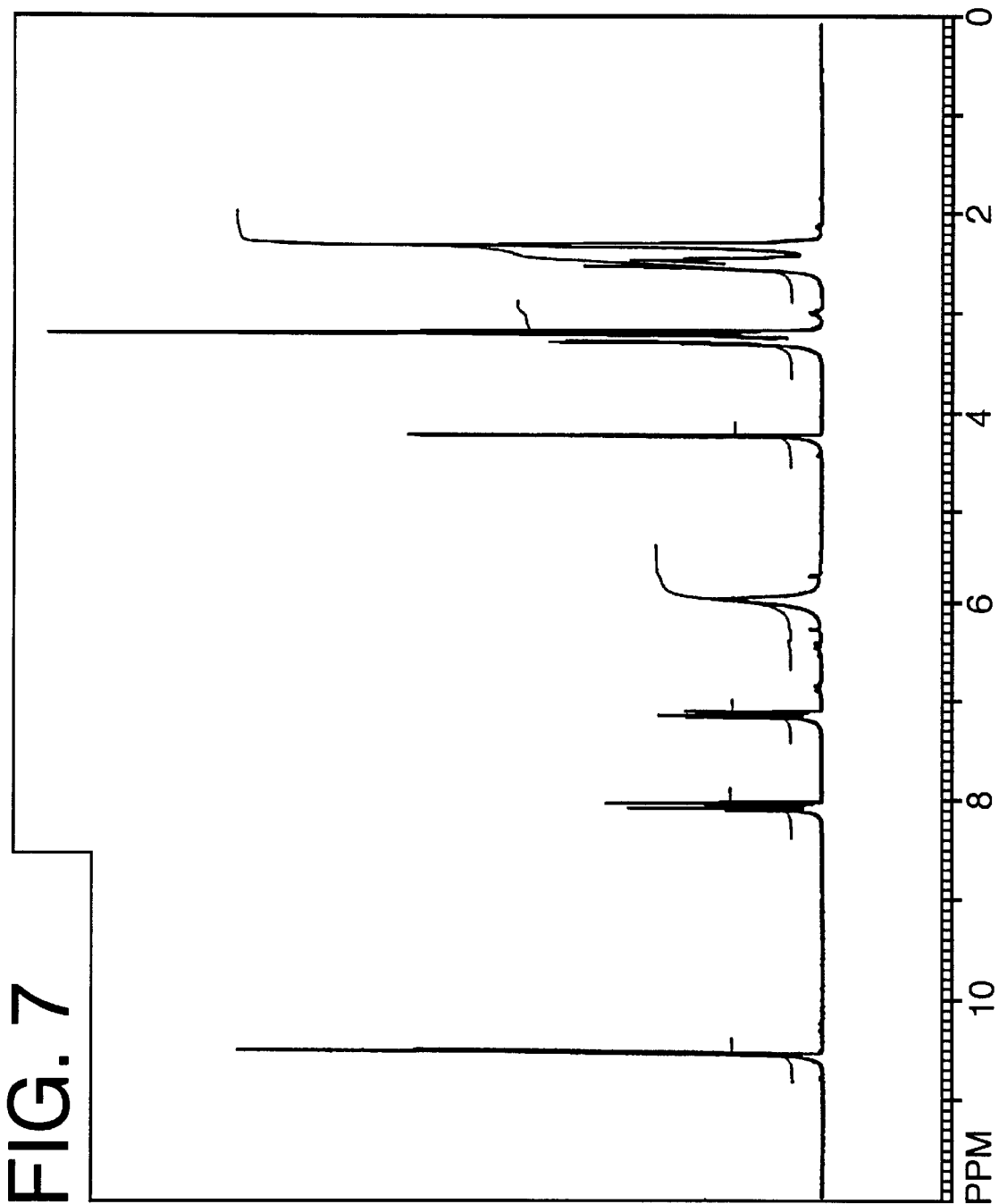

FIG. 7 is the NMR spectrum for the compound having the structure:

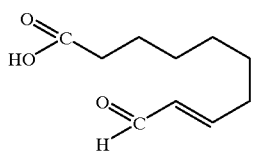

used in the process of Example XIII.

Figure 8:
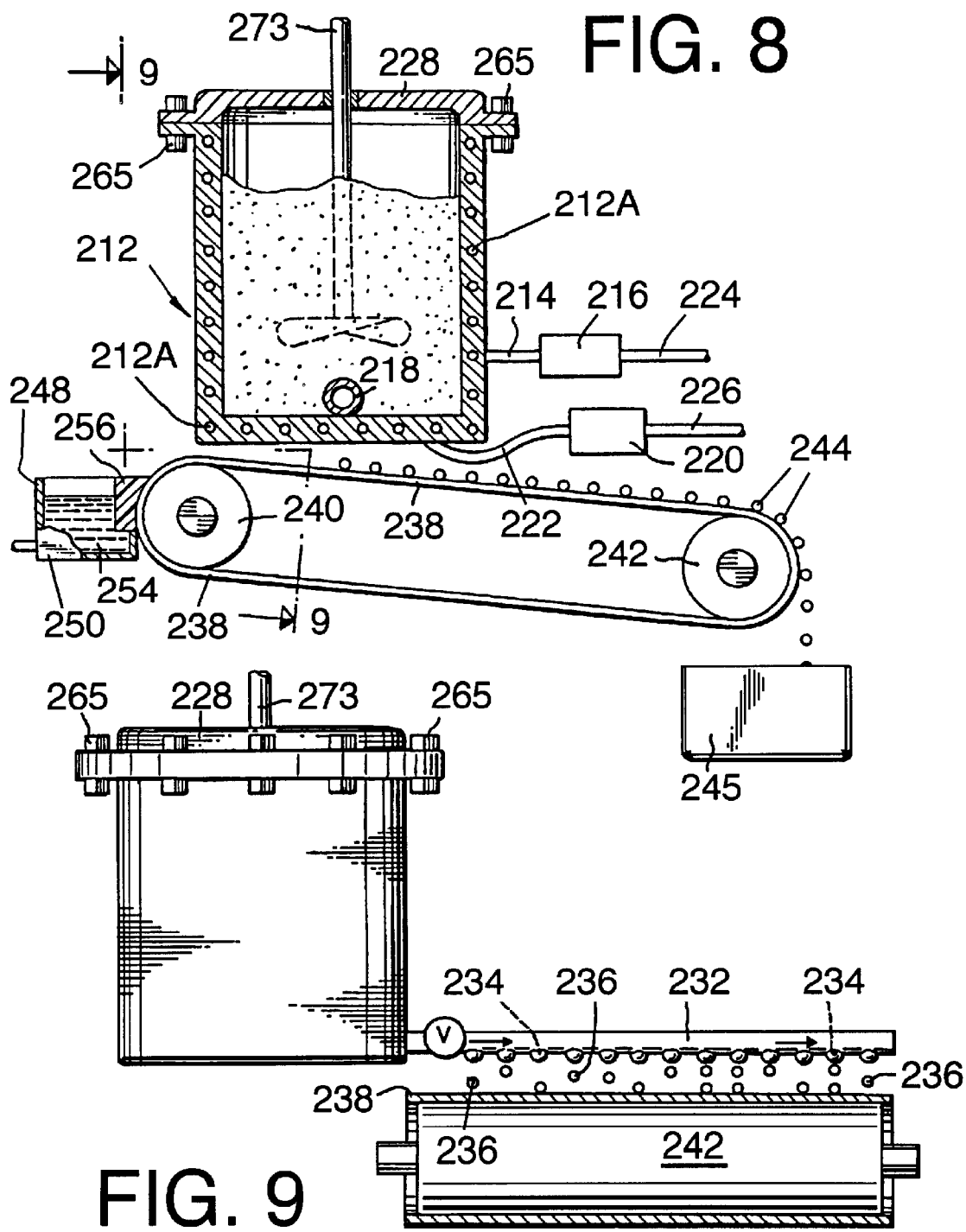

FIG. 8 represents a cutaway side elevation view of apparatus used in forming perfumed polymers which contain embedded therein at least one of the jasmonic acid derivative-containing compositions of our invention.

Figure 9:
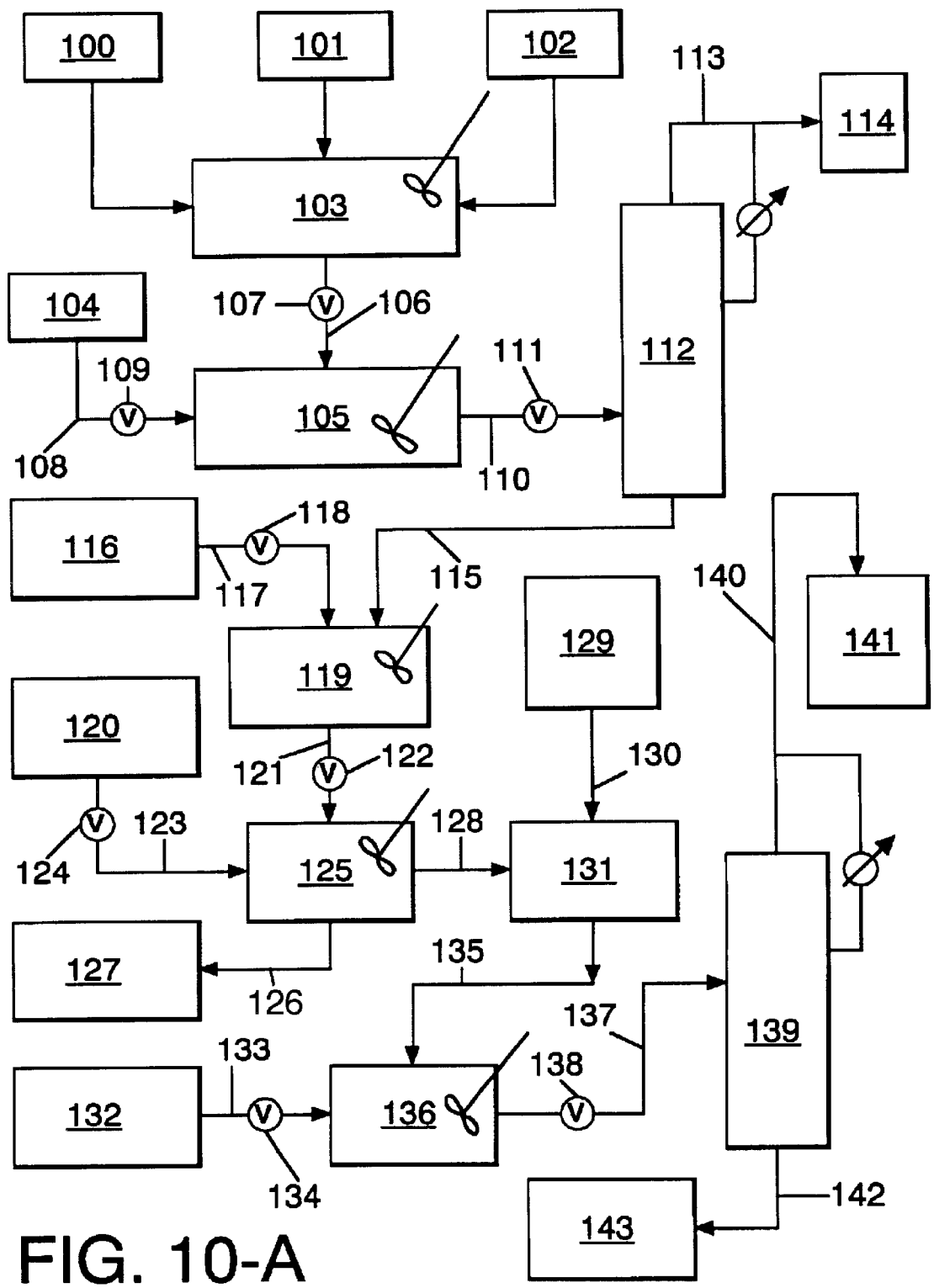

FIG. 9 is a front view of the apparatus of FIG. 8 looking in the direction of the arrows.

Figure 10:
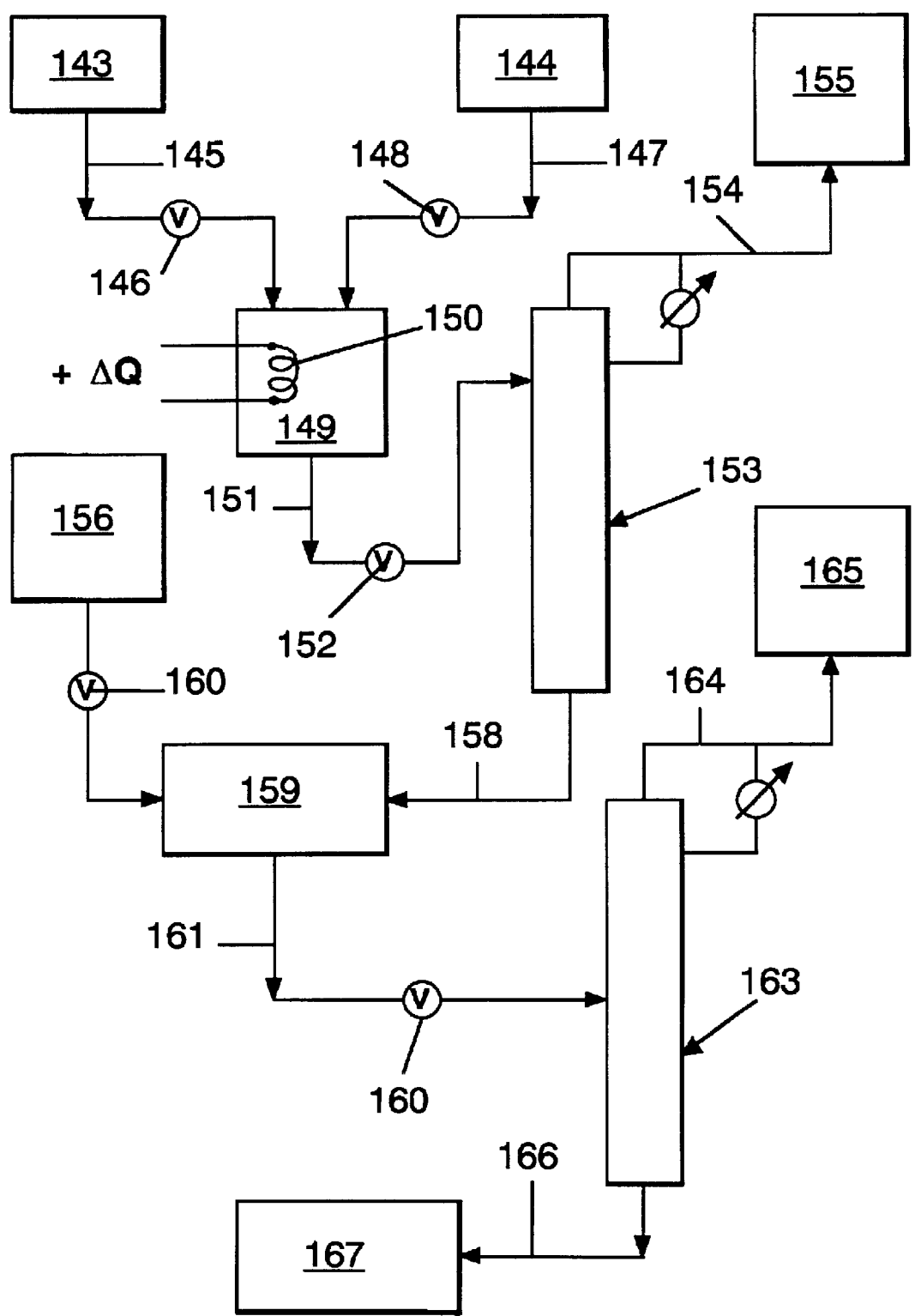

FIG. 10A is a schematic block flow diagram showing process steps for preparing pure jasmonic acid defined according to the structures:

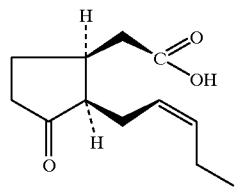

and

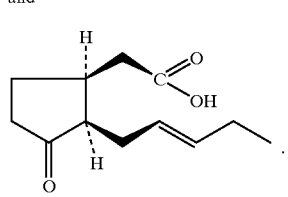

FIG. 10B is a schematic block flow diagram showing the process steps and apparatus for preparing the methyl jasmonate of our invention from the jasmonic acid of our invention according to the reactions:

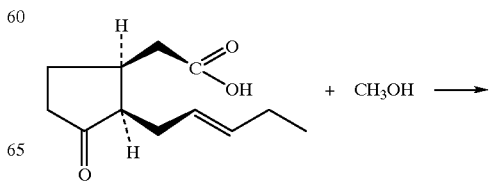

-continued

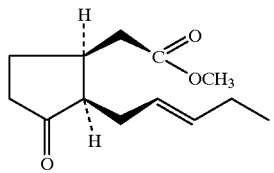

and

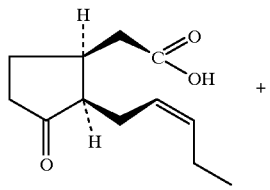 + CH₃OH ⟶

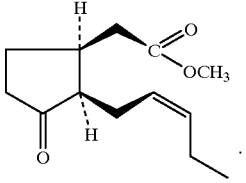

Figure 11:
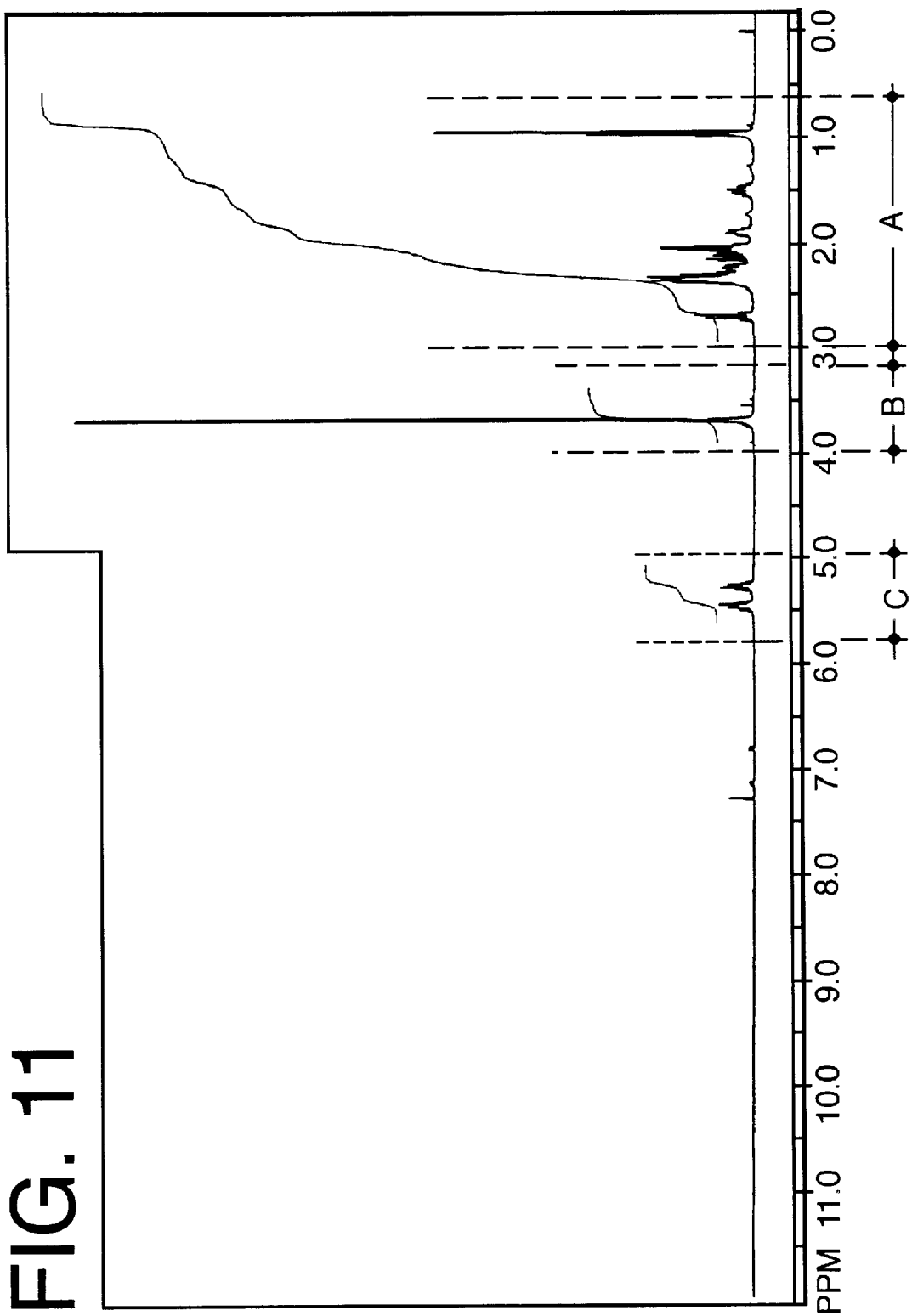

FIG. 11 is the NMR spectrum for the pure optical isomer ($\alpha_D^{20}$) of the compound having the structure:

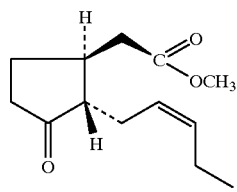

prepared according to Example XV having an optical rotation of +58°.

FIG. 11A is an enlargement of section "A" of the NMR spectrum of FIG. 11.

FIG. 11B is an enlargement of section "B" of the NMR spectrum of FIG. 11.

FIG. 11C is an enlargement of section "C" of the NMR spectrum of FIG. 11.

FIG. 12 is the mass spectrum for the reaction product of Example XV containing the compounds having the structures:

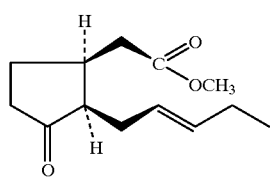

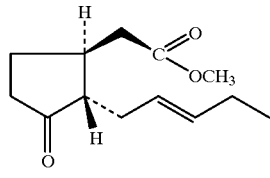

-continued

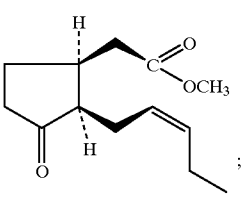

; and

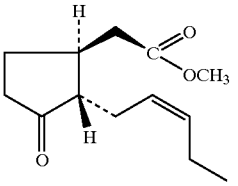

as well as the compounds having the structures:

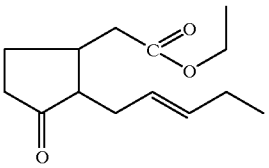

and

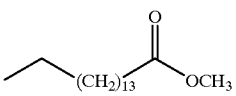

and the compound having the structure:

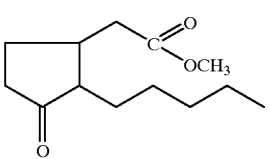

FIG. 13A is the HPLC profile for the optical isomer having the structure:

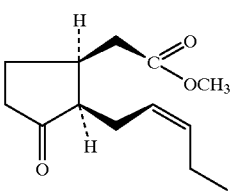

prepared according to Example XV (optical rotation ($\alpha_D^{20}$)=+580) (conditions: OV1 column).

FIG. 13B is the HPLC profile for the optical isomer ($\alpha_D^{20}$=+58°) having the structure:

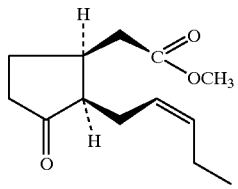

prepared according to Example XV (conditions: Carbowax column).

Figure 14:
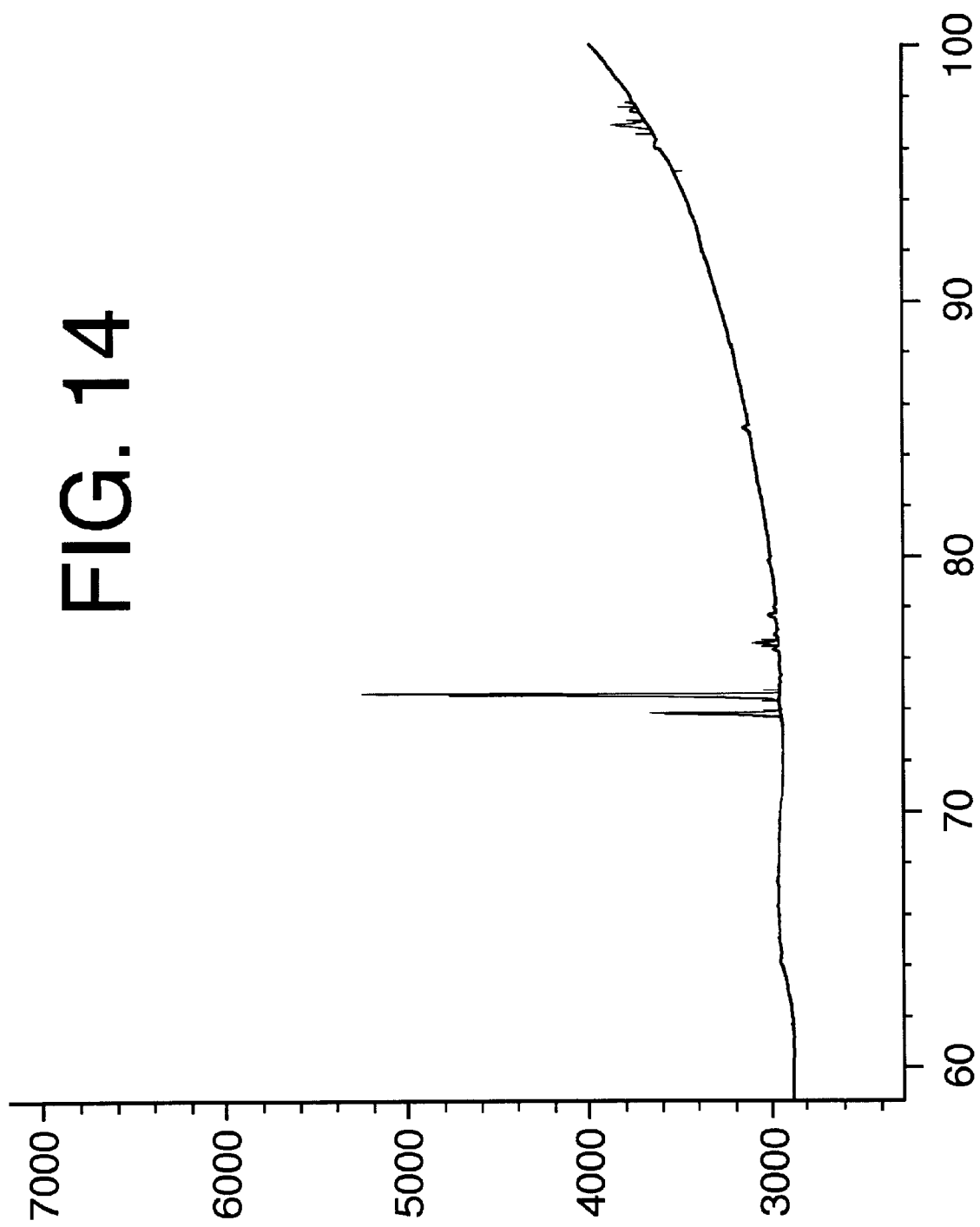

FIG. 14 is the HPLC profile (chiral column) for the optical isomer ($\alpha_D^{20}$=+58°) of the compound having the structure:

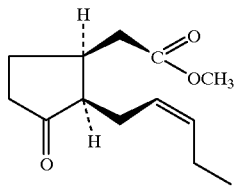

produced according to Example XV.

Figure 15:
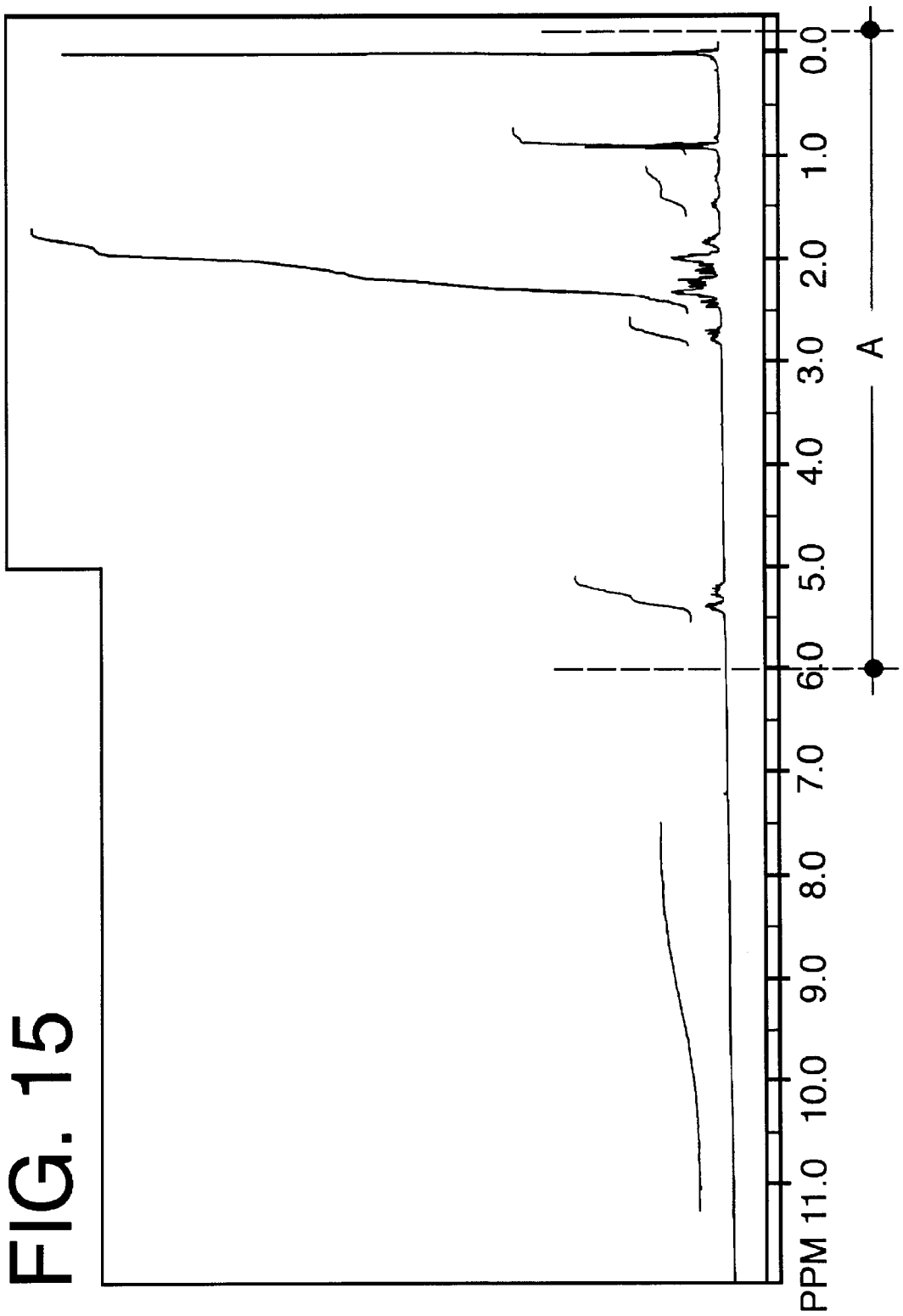

FIG. 15 is the NMR spectrum for the compound having the structure:

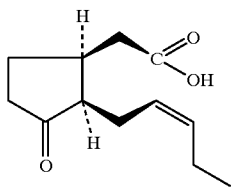

(optical isomer: ($\alpha_D^{20}$=+58°) prepared according to Example VI.

FIG. 15A is an enlargement of section "A" of the NMR spectrum of FIG. 15.

DETAILED DESCRIPTION OF THE DRAWINGS

Figure 1:
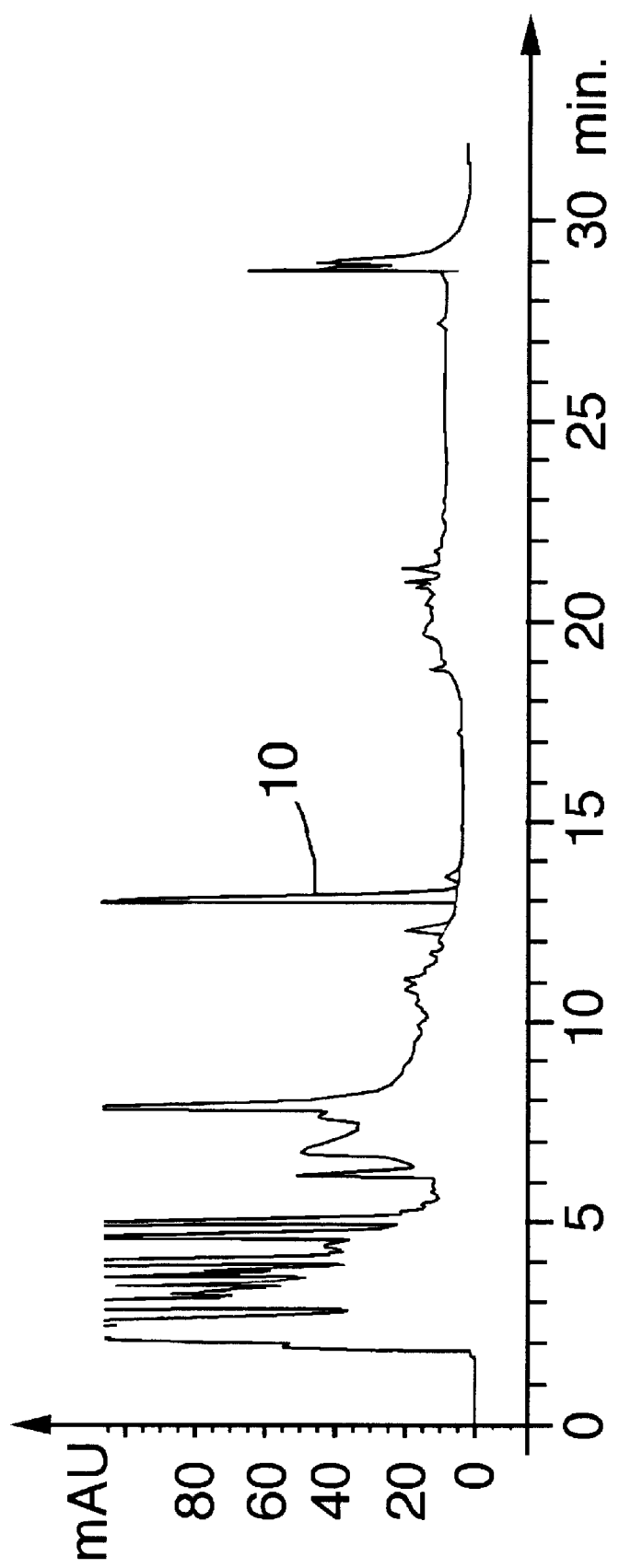
FIG. 1 is the HPLC profile for the reaction product of Example XIII (conditions: 250 mm×4.6 mm ZORBAX® SB-C18 column).

Referring to FIG. 1, the peak indicated by reference numeral 10 is the peak for the jasmonic acid isomer defined according to the structure:

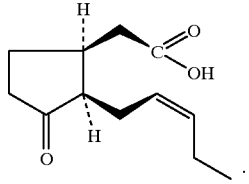

Figure 2:
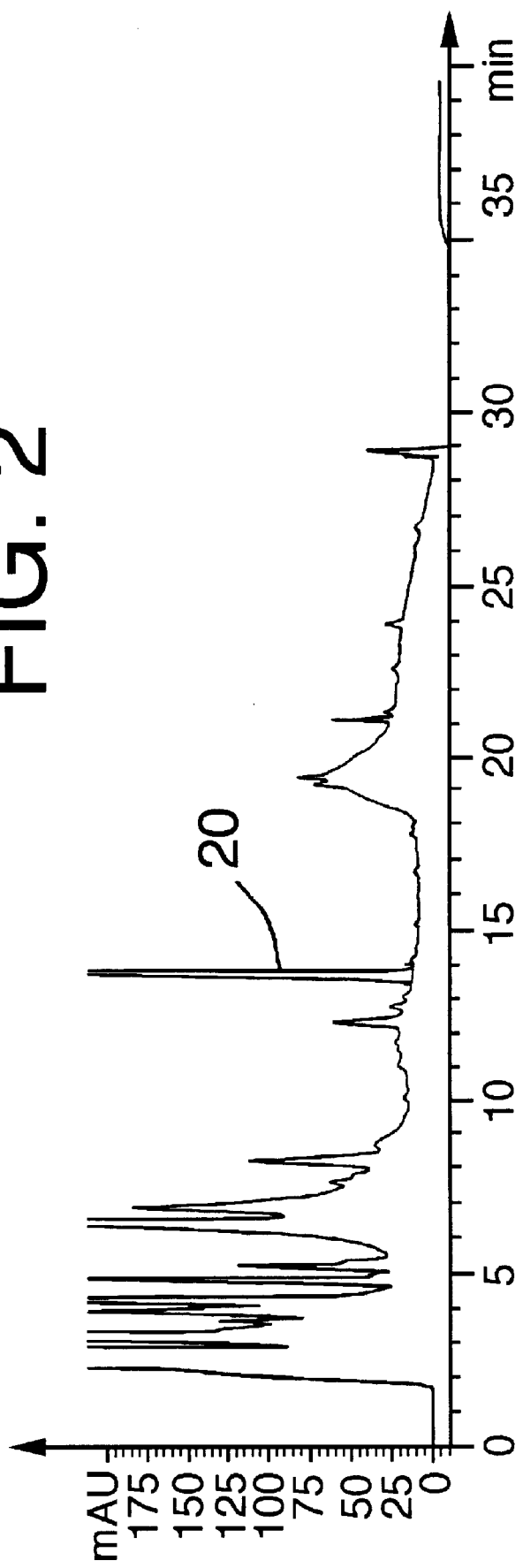
FIG. 2 is the HPLC profile for the reaction product of Example XIV (conditions: 250 mm×4.6 mm ZORBAX® SB-C18 column).

Referring to FIG. 2, the peak indicated by reference numeral 20 is the peak for the jasmonic acid defined according to the structure:

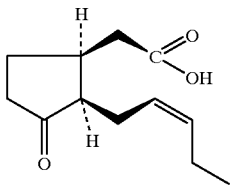

Figure 3:
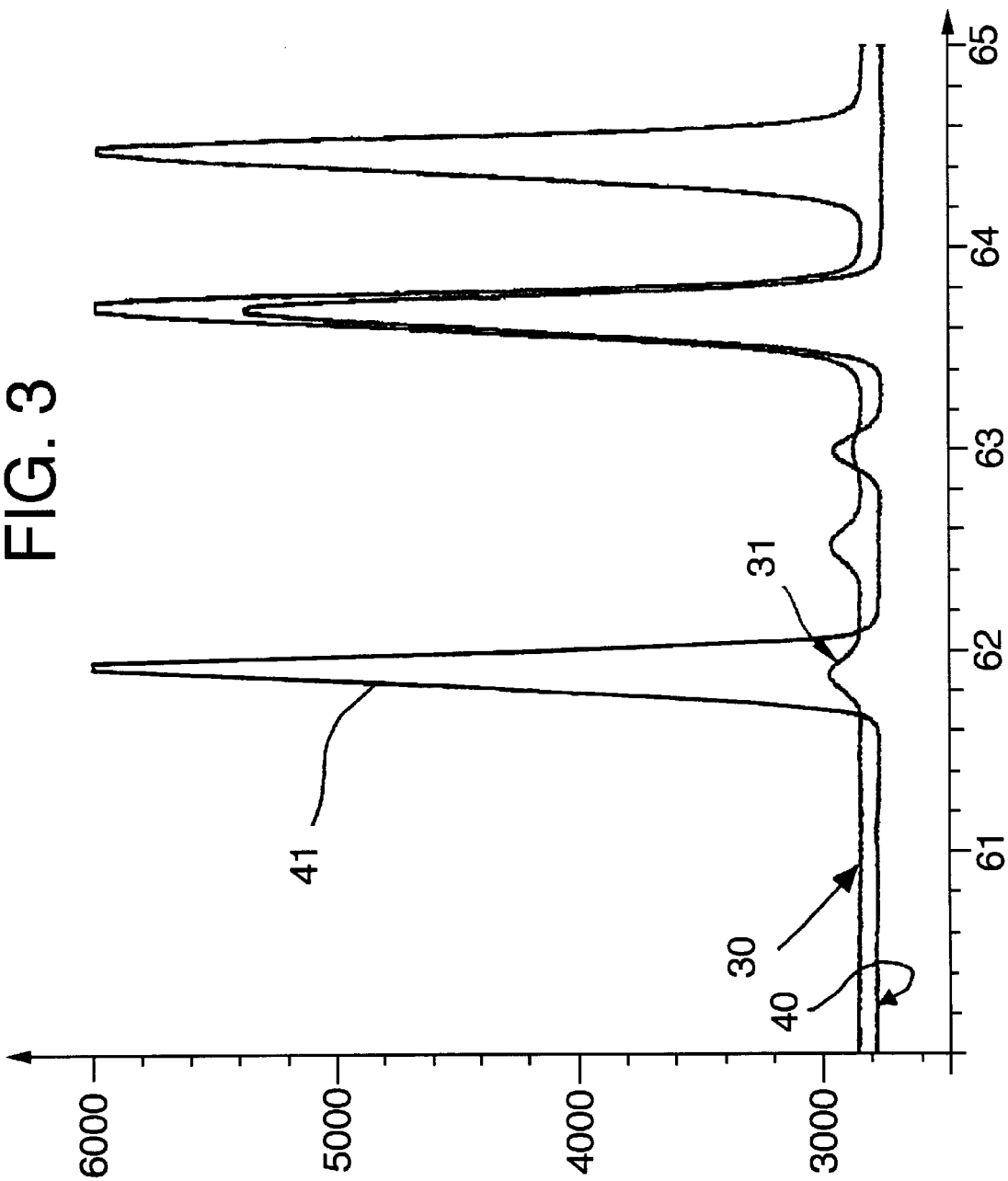
FIG. 3 is the HPLC profile for the reaction products of Example XV having the structures.

Referring to FIG. 3, the peak indicated by reference numeral 41 is the peak for the isomer having the structure:

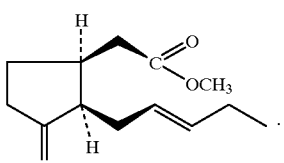

The peak indicated by reference numeral 31 is for the isomer having the structure:

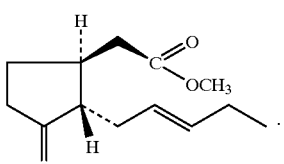

The curve for the material containing the isomer having the structure:

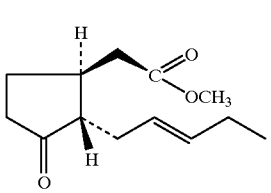

is indicated by reference numeral 30. The curve for the material containing the isomer shaving the structure:

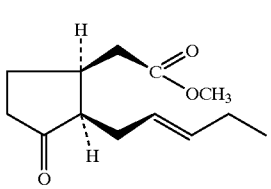

is indicated by reference numeral 40.

Referring to FIG. 5B, the peak indicated by reference numeral 50 is the peak for the isomer having the structure:

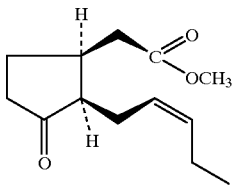

The peaks indicated by reference numerals 51 and 52 are for the isomer having the structure:

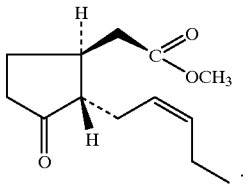

Referring to FIGS. 8 and 9, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus referring to FIGS. 8 and 9, in particular, the apparatus used in producing such elements comprises a device for forming the polymer containing perfume, e.g., polyethylene or polyethylene-polyvinyl acetate of mixtures of same or polypropylene, which comprises a vat or container 1212 into which the polymer taken alone or in admixture with other polymers in the perfuming substance which is at least one of the jasmonic acid derivative(s) of our invention or mixtures of jasmonic acid derivatives and other compatible perfume components is placed. The container is closed by means of an airtight lid 1228 and clamped to the container by bolts 1265. A stirrer 1273 traverses the lid or cover 1228 in an airtight manner and is rotatable in a suitable manner. A surrounding cylinder 1212A having heating coils which are supplied with electric current through cable 1214 from a rheostat or control 1216 is operated to maintain the temperature inside the container 1212 such that the polymer in the container will be maintained in the molten or liquid state. It has been found advantageous to employ polymers at such a temperature that the viscosity will be in the range of 90–100 Saybolt seconds. The heater 1218 is operated to maintain the upper portion of the container 1212 within a temperature range of, for example, 220–270° C. in the case of low density polyethylene. The bottom portion of the container 1212 is heated by means of heating coils 1212A regulated through the control 1220 connected thereto through a connecting wire 1222 to maintain the lower portion of the container 1212 within a temperature range of 220–270° C.

Thus, the polymer or mixture of polymers added to the container 1212 is heated from 10–12 hours, whereafter the perfume composition or perfume material which contains one or more of the jasmonic acid derivatives of our invention is quickly added to the melt. Generally, about 10–45% by weight of the resulting mixture of the perfumery substance is added to the polymer.

After the perfume material is added to the container 1212, the mixture is stirred for a few minutes, for example, 5–15 minutes, and maintained within the temperature ranges indicated previously by the heating coil 1212A. The controls 1216 and 1220 are connected through cables 1224 and 1226 to a suitable supply of electric current for supplying the power for heating purposes.

Thereafter, the valve "V" is opened, permitting the mass to flow outwardly through conduit 1232 having a multiplicity of orifices 1234 adjacent to the lower side thereof. The outer end of the conduit 1232 is closed so that the liquid polymer in intimate admixture with one or more of the jasmonic acid derivatives of our invention or mixture of perfume substance and one or more of the jasmonic acid derivatives of our invention, will continuously drop through the orifices 1234 downwardly from the conduit 1232. During this time, the temperature of the polymer intimately admixed with the perfumery substance in the container 1212 is accurately controlled so that a temperature in the range of from about 240–250° C. (for example, in the case of low density polyethylene) will exist in the conduit 1232. The regulation of the temperature through the controls 1216 and 1220 is essential in order to insure temperature balance to provide for the continuous dropping or dripping of molten polymer intimately admixed with the perfume substance which is all or which contains one or more of the jasmonic acid derivatives of our invention, through the orifices 1234 at a rate which will insure the formation of droplets 1236 which will fall downwardly onto a moving conveyor belt 1238 caused to run between conveyor wheels 1240 and 1242 beneath the conduit 1232.

When the droplets 1236 fall onto the conveyor 1238, they form pellets 1244 which harden almost instantaneously and fall off the end of the conveyor 1238 into a container 1245 which is advantageously filled with water or some other suitable cooling liquid to insure the rapid cooling of each of the pellets 1244. The pellets 1244 are then collected from the container 1245 and utilized for the formation of other functional products, e.g., garbage bags and the like.

Belt 1238 is continuously moistened with sponge-like material 1256 supplied with water 1254 from container 1250 having sidewall 1248 so that the belt is continuously cooled.

Referring to FIG. 10A, carbon source (e.g., glucose) from location 102 is admixed with nutrient (containing, for example, magnesium sulfate heptahydrate and sodium nitrate) from location 101 and culture (containing at least one strain of *Diplodia gossypina*) from location 100 are admixed and placed in fermenter 103. The fermenter is run, for example, for a period of 10 days, and the resulting product is then passed through line 106 past valve 107 into mixing vessel 105 and combined with extraction solvent (e.g., ethyl acetate) from location 104. The resulting mixture is then separated and the solvent/jasmonic acid material is passed through line 110 past valve 111 into distillation column 112 where overhead solvent is distilled through line 113 and recovered at location 114, and crude jasmonic acid (bottoms) is passed into vessel 119 where it is admixed with aqueous sodium carbonate solution from location 116 which is passed through line 117 past valve 118. The resulting sodium carbonate solution/jasmonic acid material is then passed through line 121 past valve 122 and mixed with extraction solvent from location 120 which is passed through line 123 past valve 124 and admixed with such extraction solvent in vessel 125. The organic phase is then passed to location 127 through line 126, and the aqueous phase is passed through line 128 into vessel 131 where it is admixed with phosphoric acid from location 129 (pH adjustment). The resulting product is then further mixed with extraction solvent from location 132 which is passed through line 133 past valve 134 and admixed in vessel 136. The resulting organic phase is separated from the aqueous phase and passed through line 137 past valve 138 into distillation column 139 where the recovered solvent (overhead) is passed through line 140 into solvent recovery system 141, and the resulting pure jasmonic acid (bottoms) is passed through line 142 into location 143 (structure:

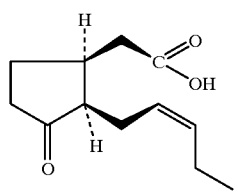

and/or

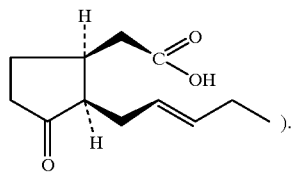

).

Referring to FIG. 10B, jasmonic acid having the structure:

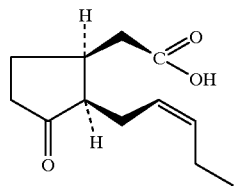

and/or

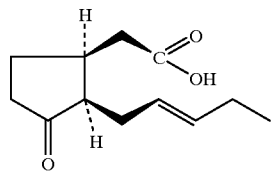

(from the apparatus of FIG. 10A) at location 143 is passed through line 145 past valve 146 into autoclave 149 where it is admixed with methanol from location 144 which is passed through line 147 past valve 148 into autoclave 149. Autoclave 149 is heated under pressure using heating element 150 causing the reactions:

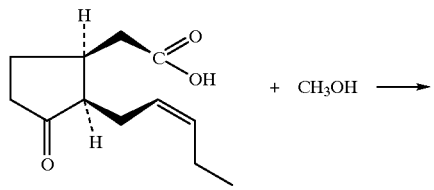

-continued

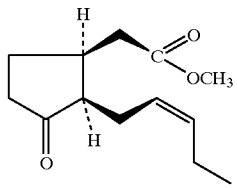

and

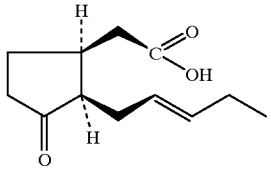 + CH₃OH ⟶

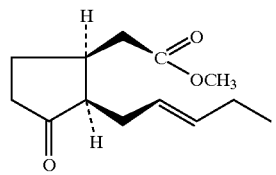

to take place thereat. The resulting products (crude) having the structures:

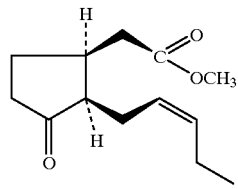

and

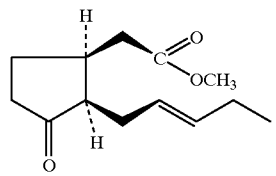

are then passed through line 151 past valve 152 into distillation column 153, where the excess methanol is recovered overhead via line 154 into recovery system 155, and the resulting crude methyl jasmonate products are admixed with extraction solvent from location 156, passed through line 157 past valve 160 into vessel 159. The extraction solvent/ crude methyl jasmonate is then mixed and passed through line 161 past valve 162 into distillation column 163, where solvent is recovered overhead via line 164 into solvent recovery system 165, and purified methyl jasmonate (bottoms) is passed into vessel 167, the purified methyl jasmonate having the structures:

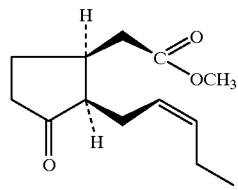

-continued and/or

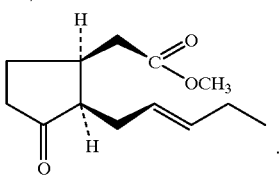

Referring to FIG. 12, the GC mass spectrum for the crude reaction product of Example XV contains the following peaks:

(a) the peak indicated by reference numeral 120 is the peak for the compound having the structure:

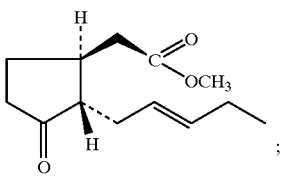

(b) the peak indicated by reference 121 is the peak for the compound having the structure:

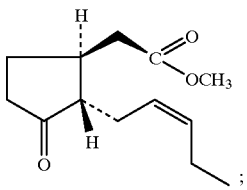

(c) the peak indicated by reference numeral 121 also contains a side peak for the compound having the structure:

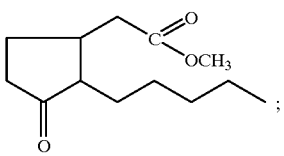

(d) the peaks indicated by reference numerals 122 and 123 are for compounds having the structures:

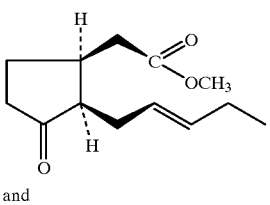

and

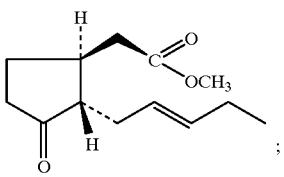

(e) the peak indicated by reference numeral 124 is for the compound having the structure:

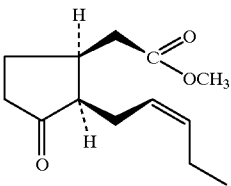

(f) peaks indicated by reference numerals 125A and 125B are for compounds defined according to the structure:

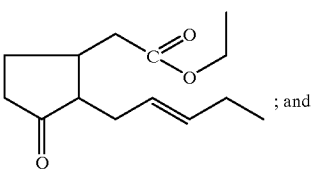

; and (g) the peak indicated by reference numeral 126 is for the compound having the structure:

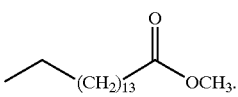

* * * * *

The following examples are given to illustrate embodiments of the invention as it is preferred to practice it. It will be understood that these examples are illustrative, and the invention is not to be considered as restrictive thereto except as indicated in the appended claims.

All parts, proportions, percentages and ratios hereinafter referred to are by weight unless otherwise indicated.

EXAMPLE I

Jasmonic Acid Screening Procedure

| Medium 5059H | |
|---|---|
| $KH_2PO_4$ | 1.0 gm |
| $MgSO_4 \cdot 7H_2O$ | 0.5 gm |
| Yeast extract | 1.0 gm |
| Soy peptone | 5.0 gm |
| Trace minerals | 10.0 ml |
| Dextrose | 30.0 gm |
| Deionized water | 1.0 L |
| pH adjusted to 5.5 before sterilization | |

| Trace Minerals Solution 5059H | |
|---|---|
| $FeSO_4 \cdot 7H_2O$ | 10.0 mg |
| $ZnSO_4 \cdot 7H_2O$ | 8.8 mg |
| $CuSO_4 \cdot 5H_2O$ | 15.0 mg |
| $MnSO_4 \cdot H_2O$ | 7.6 mg |

-continued

| Trace Minerals Solution 5059H | |
|---|---|
| $(NH_4)_6Mo_7O_{24}\cdot 4H_2O$ | 10.0 mg |
| Deionized water | 1.0 L |

Procedure

500 Ml flasks containing 100 ml of broth were inoculated from slant stock cultures (PDA) and incubated at 25° C. stationary or at 150 rpm. Flask cultures were periodically analyzed by acidifying a 1 ml sample, extracting with 1 ml of ethyl acetate, centrifuging, concentrating and spotting on TLC plates. Alternately, a whole flask culture was xtract used to prepare the methyl ester and followed by GC analysis.

| TLC Solvents | |
|---|---|
| Ethyl acetate | 50% |
| Hexanes | 50% |
| Acetic acid | 0.5% |

TABLE I

| | | Jasmonic Acid (mg/L) | | | |
|---|---|---|---|---|---|
| Microorganisms | ATCC | Stationary | Incubation Time (Days) | Shake | Incubation Time (Days) |
| Diplodia gossypina | 10936 | 210 | 7 | 1.1 | 7 |
| Diplodia gossypina | 16391 | Neg | 7 | 5.6 | 7 |
| Diplodia gossypina | 20575 | Neg | 7 | Neg | 7 |
| Diplodia gossypina | 20576 | Neg | 7 | Neg | 7 |
| Diplodia gossypina | 22644 | Neg | 7 | Neg | 7 |
| Diplodia gossypina | 26123 | 23 | 7 | Neg | 7 |

TABLE II

| | | Jasmonic Acid (TLC) | | | |
|---|---|---|---|---|---|
| Microorganisms | | Stationary | Incubation Time (Days) | Shake | Incubation Time (Days) |
| Diplodia gossypina | ATCC 28570 | | | Neg | 9 |
| Diplodia gossypina | ATCC 34643 | | | + | 9 |
| Diplodia gossypina | ATCC 36037 | | | + | 9 |
| Diplodia gossypina | ATCC 76087 | | | + | 9 |
| Lasiodiplodia theobromae | IFO 31643 | | | + | 5 |
| Botryosphaeria rhodina | CBS 110.11 | | | Neg | 7 |
| Botryosphaeria rhodina | CBS 124.13 | | | Neg | 7 |
| Botryosphaeria rhodina | CBS 174.26 | | | Neg | 7 |
| Botryosphaeria rhodina | CBS 175.26 | | | Neg | 7 |
| Botryosphaeria rhodina | CBS 176.26 | | | Neg | 7 |
| Botryosphaeria rhodina | CBS 190.73 | Neg | 10 | | |
| Botryosphaeria rhodina | CBS 230.30 | | | Neg | 7 |
| Botryosphaeria rhodina | CBS 287.47 | | | + | 7 |
| Botryosphaeria rhodina | CBS 301.36 | | | Neg | 7 |
| Botryosphaeria rhodina | CBS 304.79 | | | + | 5 |
| Botryosphaeria rhodina | CBS 306.58 | | | Neg | 5 |
| Botryosphaeria rhodina | CBS 356.59 | | | Neg | 5 |
| Botryosphaeria rhodina | CBS 374.54 | | | Neg | 10 |
| Botryosphaeria rhodina | CBS 456.78 | | | Neg | 10 |
| Botryosphaeria rhodina | CBS 494.78 | | | Neg | 10 |
| Botryosphaeria rhodina | CBS 495.78 | | | Neg | 10 |

| Medium 5074H | |
|---|---|
| $NaNO_3$ | 2.0 gm |
| $KH_2PO_4$ | 1.0 gm |
| $MgSO_4\cdot 7H_2O$ | 0.5 gm |
| KCl | 0.5 gm |
| $FeSO_4\cdot 7H_2O$ | 10.0 mg |
| Yeast extract | 1.0 gm |
| Trace minerals | 1.0 ml |
| Dextrose | 50.0 gm |
| Deionized water | 1.0 L |
| pH adjusted to 5.5 before sterilization | |

| Trace Minerals Solution 5059H | |
|---|---|
| $ZnSO_4\cdot 7H_2O$ | 1.0 gm |
| $CuSO_4\cdot 5H_2O$ | 0.15 gm |
| $MnSO_4\cdot H_2O$ | 0.1 gm |
| $(NH_4)_6Mo_7O_{24}\cdot 4H_2O$ | 0.1 gm |
| Deionized water | 1.0 L |

Screening Results

TABLE III

| | | Jasmonic Acid (TLC) | | | |
|---|---|---|---|---|---|
| Microorganisms | | Stationary | Incubation Time (Days) | Shake | Incubation Time (Days) |
| Botryodiplodia theobromae | FPRL S-22L | Neg | 7 | Neg | 7 |
| Botryosphaeria rhodina | CBS 176.26 | + | 7 | + | 7 |
| Botryosphaeria rhodina | CBS 205.75 | + | 7 | − | 7 |

TABLE III-continued

| | | Jasmonic Acid (TLC) | | | |
|---|---|---|---|---|---|
| Microorganisms | | Stationary | Incubation Time (Days) | Shake | Incubation Time (Days) |
| Botryosphaeria rhodina | CBS 287.47 | + | 7 | + | 7 |
| Botryosphaeria rhodina | CBS 304.79 | + | 7 | + | 7 |

TABLE IV

NOTE: Same medium as 5074H, except pH adjusted to 9.0 before sterilization. A 72–96 hour shake flask inoculum (100 ml/500 ml flask; 150 rpm; 30° C.) was chopped in a sterile blender jar and 4 ml was used to inoculate a new flask, including the addition of 10 ml sterile 50% dextrose.

| | | Jasmonic Acid (TLC) | | | |
|---|---|---|---|---|---|
| Microorganisms | | Stationary | Incubation Time (Days) | Shake | Incubation Time (Days) |
| Diplodia gossypina | ATCC 20575 | | | + | 6 |
| Diplodia gossypina | ATCC 26123 | | | + | 7 |
| Diplodia gossypina | ATCC 36037 | | | + | 6 |
| Diplodia gossypina | ATCC 64959 | | | + | 6 |
| Botryosphaeria rhodina | CBS 287.47 | | | + | 7 |
| Botryosphaeria rhodina | CBS 304.73 | | | + | 6 |
| Lasiodiplodia theobromae | IFO 6469 | | | + | 7 |

EXAMPLE II

Screening of Microorganisms in Submerged Culture for the Production of Jasmonic Acid

| Medium: Buffered Minimal Salts Medium (bMS) | |
|---|---|
| NaNO$_3$ | 2.0 gm/L |
| KH$_2$PO$_4$ | 2.0 gm/L |
| K$_2$HPO$_4$ | 0.5 gm/L |
| MgSO$_4$-7H$_2$O | 2.0 gm/L |
| KCl | 0.5 gm/L |
| FeSO$_4$-7H$_2$O | 1.0 mg/L |
| TASTONE ® 900 | 0.5 gm/L |

After sterilization of bMS medium at 120° C. and 15 psi, 60 g/l of 50% sterile glucose solution was added.

Procedure

Inocula for all microorganisms were prepared from frozen cultures. 2 Ml of inoculum were added to 100 ml of sterile bMS medium and incubated at 28° C. and 200 rpm. The production of jasmonic acid in the cultures was monitored by TLC and HPLC analysis.

| TLC Solvents | |
|---|---|
| Hexane | 10% |
| Ethyl acetate | 90% |
| Acetic acid | 0.5% |

| Microorganisms | Jasmonic Acid Production (9 Days) |
|---|---|
| Diplodia gossypina ATCC 10936 | 648 ppm |
| Diplodia gossypina ATCC 16391 | — |
| Diplodia gossypina ATCC 20575 | 1263 ppm |
| Diplodia gossypina ATCC 22644 | — |
| Diplodia gossypina ATCC 26123 | — |
| Diplodia gossypina ATCC 34643 | — |
| Diplodia gossypina ATCC 36037 | — |
| Diplodia gossypina ATCC 64959 | — |
| Diplodia gossypina ATCC 20571 | — |
| Diplodia gossypina NRRL 13607 | — |
| Diplodia gossypina NRRL 25011 | 75 ppm |
| Diplodia gossypina ATCC 34643 | 503 ppm |
| Botryodiplodia theobromae D7/2 (German Patent Stain) | 337 ppm |

EXAMPLE III

Screening of Microorganisms for the Production of Jasmonic Acid in Submerged Culture Under Reduced Nitrogen Levels

| Medium: Buffered Minimal Salts Medium (bMS) | |
|---|---|
| NaNO$_3$ | 0.5 gm/L |
| KH$_2$PO$_4$ | 2.0 gm/L |
| K$_2$HPO$_4$ | 0.5 gm/L |
| MgSO$_4$-7H$_2$O | 2.0 gm/L |
| KCl | 0.5 gm/L |
| FeSO$_4$-7H$_2$O | 1.0 mg/L |
| TASTONE ® 900 | 0.5 gm/L |

Following sterilization of bMS medium at 120° C. and 15 psi, 60 g/l of 50% sterile glucose solution was added.

Procedure

Inocula for all microorganisms were prepared from frozen cultures. 2 Ml of inoculum were added to 100 ml of sterile bMS medium and incubated at 28° C. and 200 rpm. The production of jasmonic acid in the cultures was monitored by TLC and HPLC analysis.

| TLC Solvents | |
|---|---|
| Hexane | 10% |
| Ethyl acetate | 90% |
| Acetic acid | 0.5% |

| Microorganisms | Jasmonic Acid Production (7 Days) |
|---|---|
| *Botryodiplodia rhodina* CBS 110.1 | − |
| *Botryodiplodia rhodina* CBS 124.13.1 | − |
| *Botryodiplodia rhodina* CBS 175.26 | − |
| *Botryodiplodia rhodina* CBS 176.25 | 44 ppm |
| *Botryodiplodia rhodina* CBS 190.73 | + |
| *Botryodiplodia rhodina* CBS 287.47 | + |
| *Botryodiplodia rhodina* CBS 289.56 | − |
| *Botryodiplodia rhodina* CBS 304.79 | + |
| *Botryodiplodia rhodina* CBS 306.58 | + |
| *Botryodiplodia rhodina* CBS 356.59 | − |
| *Botryodiplodia rhodina* CBS 374.54 | − |
| *Botryodiplodia rhodina* CRS 447.62 | + |
| *Botryodiplodia rhodina* CBS 456.78 | − |
| *Botryodiplodia rhodina* CBS 494.78 | − |
| *Botryodiplodia rhodina* CBS 495.78 | − |
| *Botryodiplodia rhodina* CBS 559.7 | + |
| *Diplodia gossypina* ATCC 36037 | 417 ppm |
| *Diplodia gossypina* ATCC 58760 | 95 ppm |
| *Diplodia gossypina* ATCC 76087 | + |

EXAMPLE IV

Production of Jasmonic Acid in Stationary Fernbach Flask Culture

Reactions:

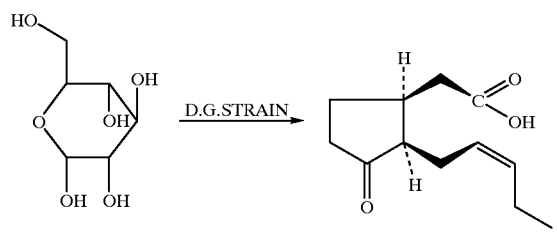

and

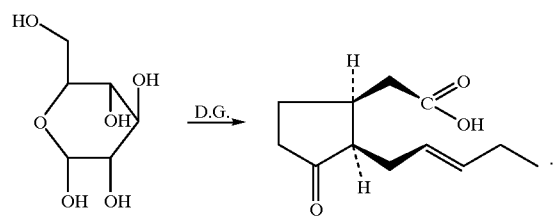

Medium

| Medium 5074H | |
|---|---|
| $KH_2PO_4$ | 1.0 gm |
| $MgSO_4 \cdot 7H_2O$ | 0.5 gm |
| Yeast extract | 1.0 gm |
| Soy peptone | 5.0 gm |
| Trace minerals | 10.0 ml |
| Dextrose | 30.0 gm |
| Deionized water | 1.0 L |
| pH adjusted to 9.0 before sterilization | |

| Trace Minerals Solution 5074H | |
|---|---|
| $FeSO_4 \cdot 7H_2O$ | 10.0 mg |
| $ZnSO_4 \cdot 7H_2O$ | 8.8 mg |
| $CuSO_4 \cdot 5H_2O$ | 15.0 mg |
| $MnSO_4 \cdot H_2O$ | 7.6 mg |
| $(NH_4)_6Mo_7O_{24} \cdot 4H_2O$ | 10.0 mg |
| Deionized water | 1.0 L |

Procedure

Inoculum:

A 500 ml Erlenmeyer flask containing 100 ml of the above medium was inoculated with *Diplodia gossypina* ATCC 10936, using a stock slant culture. 10 Ml of sterile 50% dextrose were added and the flask was incubated for 72 hours at 30° C. and 150 rpm.

Production:

500 Ml of the above medium was added to a 2.8 liter Fembach flask and sterilized for 20 minutes at 121° C. The 72 hour inoculum was chopped in a sterile blender jar, and 10 ml were added along with 50 ml of sterile 50% dextrose to the Fernbach flask, followed by stationary incubation at 30° C.

Results

After 10 days of incubation, 402 ml of culture broth were recovered, having a titer of 1.2 gram/liter jasmonic acid as determined by HPLC.

EXAMPLE V

Production of Jasmonic Acid in Aseptic Stationary Tray Culture

Reactions:

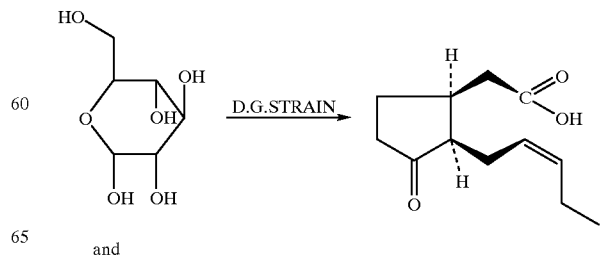

and

39

-continued

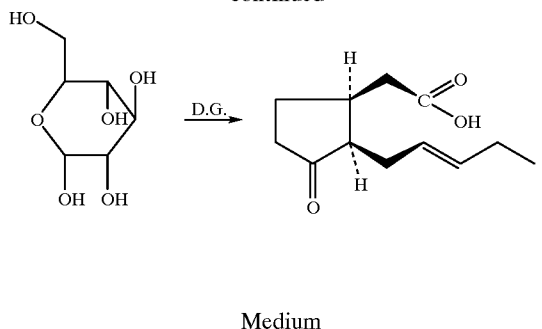

Medium

| Medium 5059H | |
|---|---|
| KH$_2$PO$_4$ | 1.0 gm |
| MgSO$_4$.7H$_2$O | 0.5 gm |
| Yeast extract | 10.0 gm |
| Soy peptone | 5.0 gm |
| Trace minerals | 10.0 ml |
| Dextrose | 30.0 gm |
| Deionized water | 1.0 L |
| pH adjusted to 8.5 before sterilization | |

| Trace Minerals Solution 5059H | |
|---|---|
| FeSO$_4$.7H$_2$O | 10.0 mg |
| ZnSO$_4$.7H$_2$O | 8.8 mg |
| CuSO$_4$.5H$_2$O | 15.0 mg |
| MnSO$_4$.H$_2$O | 7.6 mg |
| (NH$_4$)$_6$Mo$_7$O$_{24}$.4H$_2$O | 10.0 mg |
| Deionized water | 1.0 L |

Procedure

Inoculum:

A 500 ml Erlenmeyer flask containing 100 ml of the above medium was inoculated with *Diplodia gossypina* ATCC 10936, using a stock slant culture. 10 Ml of sterile 50% dextrose were added and the flask was incubated for 72 hours at 30° C. and 150 rpm.

Production:

3 Liters of sterile broth, adjusted to pH 8.5 before sterilization, were inoculated with 10 ml of a 72 hour chopped inoculum. 300 Ml of sterile 50% dextrose were added, the mixture poured into a sterile plastic tray (approximately 11 inches long, 10 inches wide and 5 inches deep) and covered with a cheesecloth/cotton screen to maintain pure culture conditions. The tray culture was incubated stationary for 14 days at 31.5° C.

Results

The culture broth had a titer of 0.71 gram/liter after 10 days of incubation. The final recovered broth (2.14 liters, 14 days) had a titer of 1.24 gram/liter as determined by HPLC.

40

EXAMPLE VI

Tray Culture Production of Jasmonic Acid

Reactions:

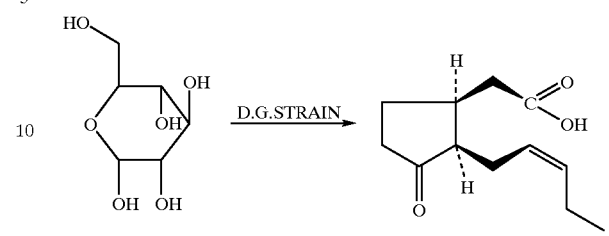

and

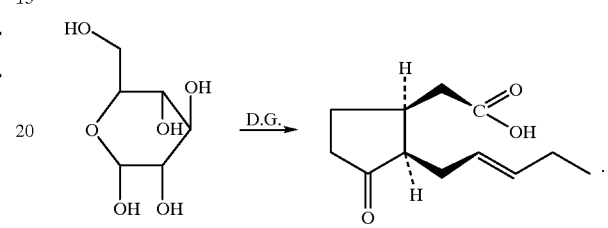

Medium

| Medium 5059H | |
|---|---|
| KH$_2$PO$_4$ | 1.0 gm |
| MgSO$_4$.7H$_2$O | 0.5 gm |
| Yeast extract | 1.0 gm |
| Soy peptone | 5.0 gm |
| Trace minerals | 10.0 ml |
| Dextrose | 30.0 gm |
| Deionized water | 1.0 L |
| pH adjusted to 9 before sterilization | |

Chloramphenicol was added after sterilization to help protect against contamination.

| Trace Minerals Solution 5059H | |
|---|---|
| FeSO$_4$.7H$_2$O | 10.0 mg |
| ZnSO$_4$.7H$_2$O | 8.8 mg |
| CuSO$_4$.5H$_2$O | 15.0 mg |
| MnSO$_4$.H$_2$O | 7.6 mg |
| (NH$_4$)$_6$Mo$_7$O$_{24}$.4H$_2$O | 10.0 mg |
| Deionized water | 1.0 L |

Procedure

Inoculum:

A 72 hour inoculum was prepared in 2.8 liter Fembach flasks, each flask containing 100 ml. The flasks were incubated at 30° C. and 150 rpm.

Production:

A total of 540 liters of broth was prepared in a 300 gallon fermenter. The pH was adjusted to 9.0, and the broth was sterilized for 30 minutes at 121° C. After cdoling to 30° C., chloramphenicol (36 grams dissolved in 600 ml ethanol), 60 liters of sterile 50% dextrose and 2,307 grams chopped inoculum (weight adjusted for a standard 45% packed cell volume) were added. After mixing for 5–10 minutes, the inoculated broth was transferred to large plastic trays (approximately 20 inches long, 17 inches wide and 5 inches deep), placed on shelves in an environmentally-controlled room. Approximately 6 liters of inoculated broth was added to each tray (total of 100 trays), the trays covered with aluminum foil and incubated stationary at 31–32° C. for 14 days. At the conclusion of incubation, the mycelial mats were filtered off, the broth was transferred to the 300 gallon fermenter and sterilized for 20 minutes at 121° C. The broth was cooled to room temperature, acidified to pH 4, and the jasmonic acid was recovered by adsorption/elution on a nonionic resin.

Results

The bulked broth (approximately 380 liters) from the 100 tray cultures had a titer of 0.895 gram/liter jasmonic acid as determined by HPLC.

EXAMPLE VII

Production of Jasmonic Acid by Combined Surface-Submerged Fermentation

Reactions:

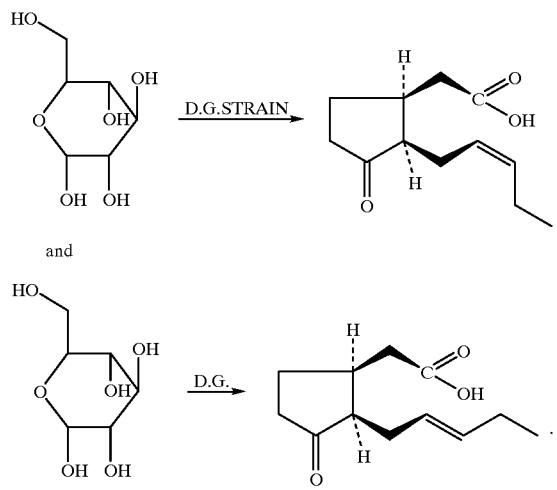

Medium

| Medium 5059H | |
|---|---|
| KH$_2$PO$_4$ | 1.0 gm |
| MgSO$_4$.7H$_2$O | 0.5 gm |
| Yeast extract | 1.0 gm |
| Soy peptone | 5.0 gm |
| Trace minerals | 10.0 ml |
| Dextrose | 30.0 gm |
| Deionized water | 1.0 L |
| pH adjusted to 9 before sterilization | |

Chloramphenicol was added after sterilization to help protect against contamination.

| Trace Minerals Solution 5059H | |
|---|---|
| FeSO$_4$.7H$_2$O | 10.0 mg |
| ZnSO$_4$.7H$_2$O | 8.8 mg |

| -continued | |
|---|---|
| Trace Minerals Solution 5059H | |
| CuSO$_4$.5H$_2$O | 15.0 mg |
| MnSO$_4$.H$_2$O | 7.6 mg |
| (NH$_4$)$_6$Mo$_7$O$_{24}$.4H$_2$O | 10.0 mg |
| Deionized water | 1.0 L |

Procedure

Inoculum:

A 500 ml Erlenmeyer flask containing 100 ml of the above medium was inoculated with *Diplodia gossypina* ATCC 10936, using a stock slant culture. 10 Ml of sterile 50% dextrose were added and the flask was incubated for 72 hours at 30° C. and 150 rpm.

Production:

A single coil of stainless steel wire cloth, having approximately ⅜ inch×⅜ inch openings, was attached vertically to the baffles of a 150 liter fermenter. Four circular wire cloth screens (same opening size) were attached to the vertical coil in horizontal positions such that the lowest screen was about one inch above the broth surface, and the other screens were separated by about one inch space between each screen. An opening in the center of each screen permitted freedom for agitation, using one impeller.

60 Liters of broth were made up and transferred to the fermenter, the pH adjusted to 9.0 and the broth sterilized at 121° C. for 30 minutes. After cooling to 30° C., 2.4 liters of chopped 72 hour inoculum, chloramphenicol (6.0 grams dissolved in 60 ml of ethanol) and 1.2 liters of sterile 50% dextrose were added. Sterile 50% dextrose solution and sterile deionized water were added as needed during the 19 day incubation at 30° C. Aeration was provided and agitation was engaged periodically to prevent the developing mycelium attached to the screens from drying out.

Results

At the conclusion of the incubation, approximately 31 liters of broth were recovered, having a titer of 185 mg/liter jasmonic acid as determined by HPLC.

EXAMPLE VIII

Production of Jasmonic Acid Using Plastic Biofilter Supports

Reactions:

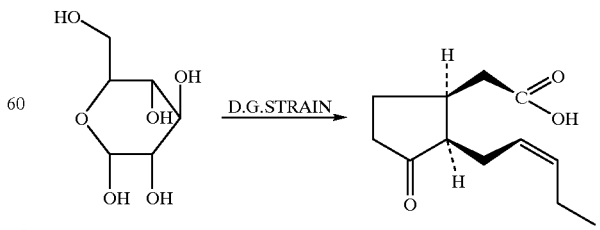

and

-continued

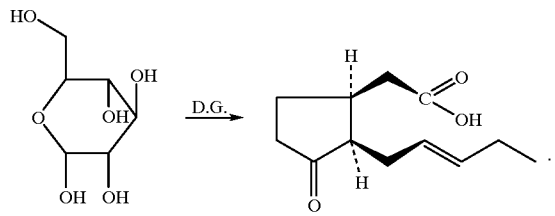

Medium

| Medium 5059H | |
|---|---|
| KH$_2$PO$_4$ | 1.0 gm |
| MgSO$_4$.7H$_2$O | 0.5 gm |
| Yeast extract | 1.0 gm |
| Soy peptone | 5.0 gm |
| Trace minerals | 10.0 ml |
| Dextrose | 30.0 gm |
| Deionized water | 1.0 L |
| pH adjusted to 9 before sterilization | |

Chloramphenicol was added after sterilization to help protect against contamination.

| Trace Minerals Solution 5059H | |
|---|---|
| FeSO$_4$.7H$_2$O | 10.0 mg |
| ZnSO$_4$.7H$_2$O | 8.8 mg |
| CuSO$_4$.5H$_2$O | 15.0 mg |
| MnSO$_4$.H$_2$O | 7.6 mg |
| (NH$_4$)$_6$Mo$_7$O$_{24}$.4H$_2$O | 10.0 mg |
| Deionized water | 1.0 L |

Procedure

Inoculum:

A 500 ml Erlenmeyer flask containing 100 ml of the above medium was inoculated with *Diplodia gossypina* ATCC 10936, using a stock slant culture. 10 Ml of sterile 50% dextrose were added and the flask was incubated for 72 hours at 30° C. and 150 rpm. The pH of the bro

EXAMPLE X

Production of Jasmonic Acid in Fernbach Flask Submerged Culture

Reactions:

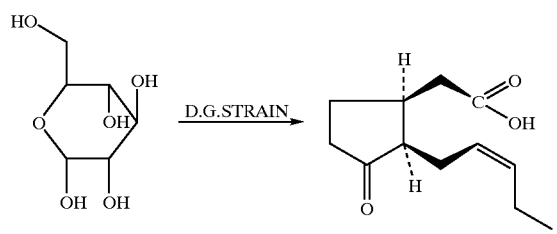

and

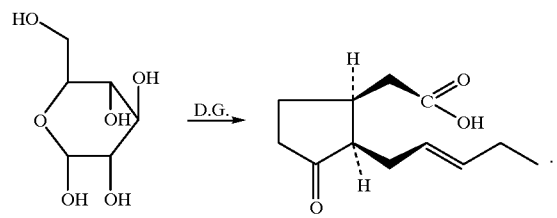

| Medium: Buffered Minimal Salts Medium (bMS) | |
|---|---|
| $NaNO_3$ | 2.0 gm/L |
| $KH_2PO_4$ | 2.0 gm/L |
| $K_2HPO_4$ | 0.5 gm/L |
| $MgSO_4$-$7H_2O$ | 2.0 gm/L |
| KCl | 0.5 gm/L |
| $FeSO_4$-$7H_2O$ | 1.0 mg/L |
| TASTONE ® 900 | 0.5 gm/L |

After sterilization of bMS medium at 120° C. and 15 psi 60 g/l of 50% sterile glucose solution was added;

Procedure

Inoculum:

A 500 ml Erlenmeyer flask containing 100 ml of sterile bMS medium was inoculated with 2 ml of a frozen chopped cell culture of *Diplodia gossypina* ATCC 10936. 6 Ml of sterile 50% dextrose were added and the flask was incubated for 3 days at 28° C. and 200 rpm. Following 3 day of incubation, the culture was chopped for 1 minute in a sterile Waring Blender and this was used as inoculum.

Production:

5 Ml of inoculum were added to 500 ml of sterile bMS medium in a Fembach flask. 30 Ml of sterile 50% dextrose were added and the flask was incubated at 28° C. and 150 rpm. The production of jasmonic acid was monitored by TLC and HPLC analyses.

Results

*Diplodia gossypina* ATCC 10936 produced jasmonic acid at a titer of 0.9 gram/liter after 8 days of incubation.

EXAMPLE XI

Production of Jasmonic Acid in Laboratory Fermenters

Reactions:

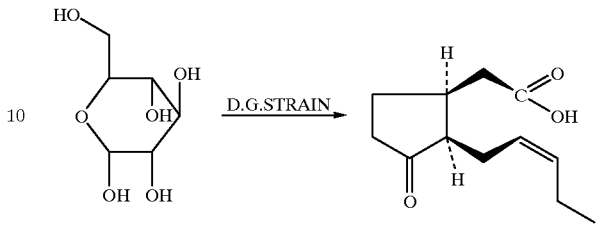

and

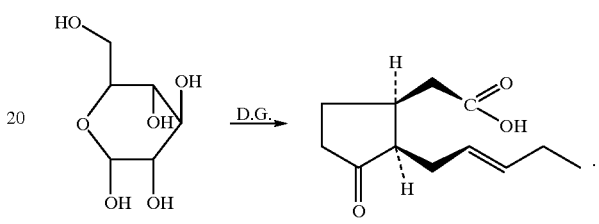

| Medium: Buffered Minimal Salts Medium (bMS) | |
|---|---|
| $NaNO_3$ | 1.0 gm/L |
| $KH_2PO_4$ | 2.0 gm/L |
| $K_2HPO_4$ | 0.5 gm/L |
| $MgSO_4$-$7H_2O$ | 2.0 gm/L |
| KCl | 0.5 gm/L |
| $FeSO_4$-$7H_2O$ | 1.0 mg/L |
| TASTONE ® 900 | 0.5 gm/L |

Following sterilization of bMS medium at 120° C. and 15 psi, 60 g/1 of 50% sterile glucose solution was added.

Procedure

Inoculum:

A 500 ml Erlenmeyer flask containing 100 ml of sterile bMS medium was inoculated with 2 ml of a frozen chopped cell culture of *Diplodia gossypina* ATCC 10936. 6 Ml of sterile 50% dextrose were added and the flask was incubated for 3 days at 28° C. and 200 rpm. Following 3 days of incubation, the inoculum was chopped for 1 minute in a sterile Waring Blender. 1 M1 of inoculum and 6 ml of sterile 50% dextrose were added to 100 ml of sterile bMS medium. After another 3 days of incubation, the whole culture was used as an inoculum for a laboratory 10 liter fermenter.

Production:

10 Liters of bMS medium containing 1 gram/liter of $NaNO_3$ was added to a 14 liter laboratory fermenter and sterilized for 30 minutes at 121° C. The above inoculum and 600 grams of sterile 50% dextrose were added to a fermenter. The fermenter was run at 28° C. and 1,000 rpm with aeration at 1 VVM and 15 psi back pressure. The pH of fermenter was maintained at 6.0 by addition of 25% NaOH. After 4 days of incubation, an additional 0.5 gram/liter aliquot of $NaNO_3$ was added. The concentration of glucose in the broth was monitored and additional sterile 50% dextrose was added to prevent glucose depletion. The production of jasmonic acid in the broth was monitored by TLC and HPLC analyses.

Results

After 13 days of incubation, *Diplodia gossypina* ATCC 10936 produced jasmonic acid at a titer of 0.85 gram/liter.

EXAMPLE XII

Production of Jasmonic Acid in Submerged 100-L Pilot Plant Fermenters

Reactions:

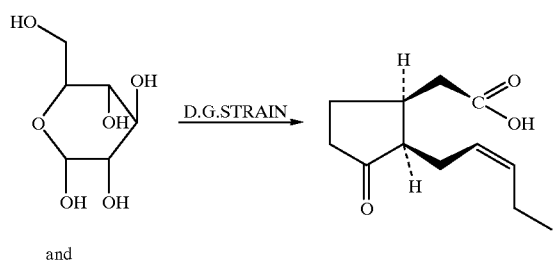

and

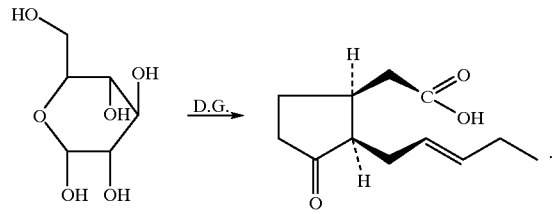

| Medium: Buffered Minimal Salts Medium (bMS) | |
|---|---|
| NaNO$_3$ | 0.5 gm/L |
| KH$_2$PO$_4$ | 2.0 gm/L |
| K$_2$HPO$_4$ | 0.5 gm/L |
| MgSO$_4$-7H$_2$O | 2.0 gm/L |
| KCl | 0.5 gm/L |
| FeSO$_4$-7H$_2$O | 1.0 mg/L |
| TASTONE ® 900 | 0.5 gm/L |

Following sterilization of bMS medium at 120° C. and 15 psi, 60 g/l of 50% sterile glucose solution was added.

Procedure

Inoculum:

A 500 ml Erlenmeyer flask containing 100 ml of sterile bMS medium was inoculated with 2 ml of a frozen chopped cell culture of *Diplodia gossypina* ATCC 10936. 6 Ml of sterile 50% dextrose were added and the flask was incubated for 3 days at 28° C. and 200 rpm. Following 3 days of incubation, the inoculum was chopped for 1 minute in a sterile Waring Blender. 5 Ml of the inoculum and 30 ml of sterile 50% dextrose were added to each of two Fembach flasks containing 500 ml of sterile bMS medium. The flasks were incubated at 28° C. and 150 rpm for 72 hours.

Production:

100 Liters of bMS containing 1 gram/liter of NaNO$_3$ were charged to a 150 liter pilot plant fermenter and sterilized for 30 minutes at 121° C. 1,000 Ml of whole inoculum and 600 grams of sterile 50% dextrose were added to the fermenter. The fermenter was run at 28° C. and 450 ml with aeration at 1 VVM and 15 psi back pressure. The pH of fermenter was maintained at 6.0 by addition of 25% NaOH. After 4 days of incubation, an additional 0.5 gram/liter aliquot of NaNO$_3$ was added. The concentration of glucose in the broth was monitored and additional sterile 50% dextrose was added to prevent glucose depletion. The production of jasmonic acid in cell culture was monitored by TLC and HPLC analyses.

Results

After 9 days of incubation, *Diplodia gossypina* ATCC 10936 produced jasmonic acid at a titer of 0.85 gram/liter.

EXAMPLE XIII

Effect of 10-oxo-8-trans-decenoic Acid on the Production of Jasmonic Acid in Fernbach Flask Submerged Culture Reactions:

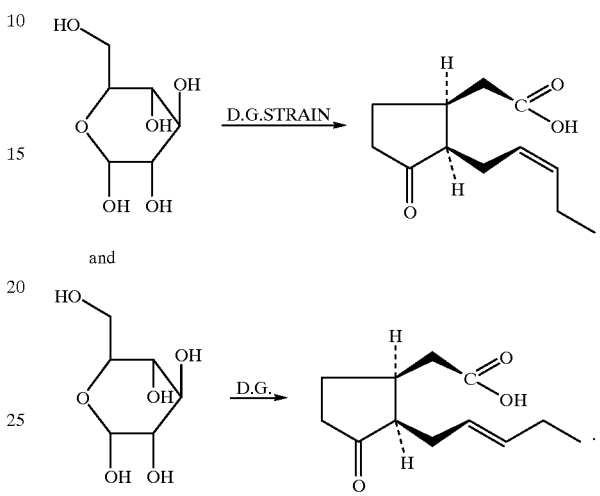

| Medium: Buffered Minimal Salts Medium (bMS) | |
|---|---|
| NaNO$_3$ | 0.5 gm/L |
| KH$_2$PO$_4$ | 2.0 gm/L |
| K$_2$HPO$_4$ | 0.5 gm/L |
| MgSO$_4$-7H$_2$O | 2.0 gm/L |
| KCl | 0.5 gm/L |
| FeSO$_4$-7H$_2$O | 1.0 mg/L |
| TASTONE ® 900 | 0.5 gm/L |

Following sterilization of bMS medium at 120° C. and 15 psi, 60 g/l of 50% sterile glucose solution was added.

Procedure

Inoculum:

A 500 ml Erlenmeyer flask containing 100 ml of sterile bMS medium was inoculated with 2 ml of a frozen chopped cell culture of *Diplodia gossypina* ATCC 10936. 6 Ml of sterile 50% dextrose were added and the flask was incubated for 3 days at 28° C. and 200 rpm. Following 3 days of incubation, the culture was chopped for 1 minute in a sterile Waring Blender and this was used as inoculum.

Production:

5 Ml of inoculum and 30 ml of sterile 50% dextrose were added to a Fernbach flask containing 500 ml of sterilize bMS medium. A stock solution of 50% 10-oxo-decenoic acid (10-ODA) in ethanol was prepared and dispensed to the flasks at a final concentration of either 1 or 10 ppm. The cultures were incubated at 28° C. and 150 rpm. The production of jasmonic acid was monitored by TLC and HPLC analyses.

Results

| Number | Flasks | 3 Days | 6 Days |
|---|---|---|---|
| 1 | Control | 106 ppm | 249 ppm |
| 2 | 1 ppm ODA | 197 ppm | 538 ppm |
| 3 | 10 ppm ODA | 279 ppm | 630 ppm |

EXAMPLE XIV

Effect of 10-oxo-8-trans-decenoic Acid on the Production of Jasmonic Acid in a Submerged 10-L of Laboratory Fermenter Reactions:

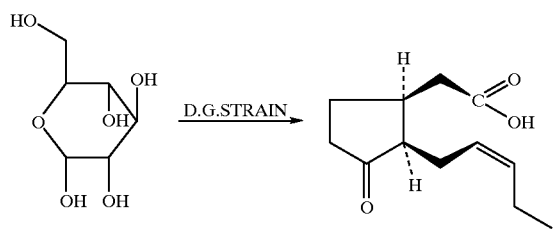

and

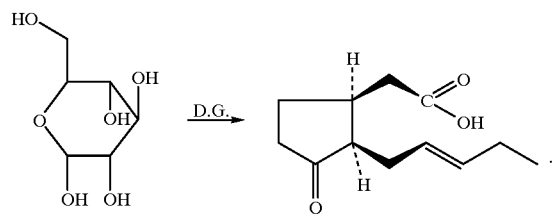

| Medium: Buffered Minimal Salts Medium (bMS) | |
|---|---|
| NaNO₃ | 2.0 gm/L |
| KH₂PO₄ | 2.0 gm/L |
| K₂HPO₄ | 0.5 gm/L |
| MgSO₄-7H₂O | 2.0 gm/L |
| KCl | 0.5 gm/L |
| FeSO₄-7H₂O | 1.0 mg/L |
| TASTONE ® 900 | 0.5 gm/L |

After sterilization of bMS medium at 120° C. and 15 psi, 60 g/l of 50% sterile glucose solution was added.

Procedure

Inoculum:

A 500 ml Erlenmeyer flask containing 100 ml of sterile bMS medium was inoculated with 2 ml of a frozen chopped cell culture of *Diplodia gossypina* ATCC 10936. 6 Ml of sterile 50% dextrose were added and the flask was incubated for 3 days at 28° C. and 200 rpm. Following 3 days of incubation, the inoculum was chopped for 1 minute in a sterile Waring Blender. 1 Ml of inoculum and 6 ml of sterile 50% dextrose were added to 100 ml of sterile bMS medium. After another 3 days of incubation, the whole culture was used as an inoculum for a laboratory 10 liter fermenter.

Production:

10 Liters of bMS containing 1.0 grams/liter of NaNO₃ were charged to a 14 liter laboratory fermenter and sterilized for 30 minutes at 121° C. 100 Ml of inoculum lated and 600 grams of sterile 50% dextrose were added to the fermenter. A stock solution of 10-ODA was prepared as in Example XIII and added to the fermenter at a final concentration of 10 ppm in the broth. The fermenter was run at 28° C. and 1,000 rpm with aeration at 1 VVM and 15 psi back pressure. The pH of fermenter was maintained at 6.0 by the addition of 25% NaOH. After 4 days of incubation, an additional 0.5 grams/liter aliquot of NaNO₃ was added. The concentration of glucose in the broth was monitored and additional sterile 50% dextrose was added to prevent glucose depletion. The production of jasmonic acid was monitored by TLC and HPLC analyses.

Results

After 11 days of incubation, *Diplodia gossypina* ATCC 10936 produced jasmonic acid at a titer of 1.5 grams/liter.

EXAMPLE XV

Production of Natural "EPI" Methyl Jasmonate-Preparation and Purification from Natural Jasmonic Acid Fermentation Broth Extract Reactions:

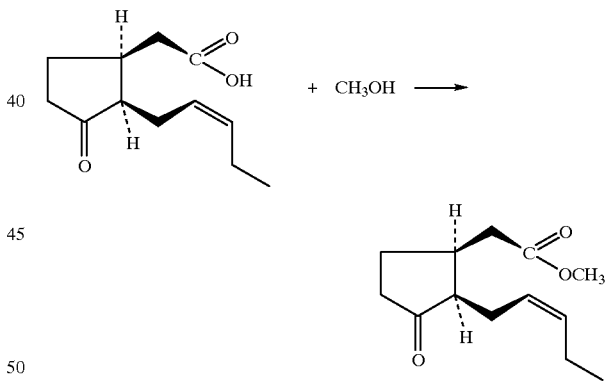

and

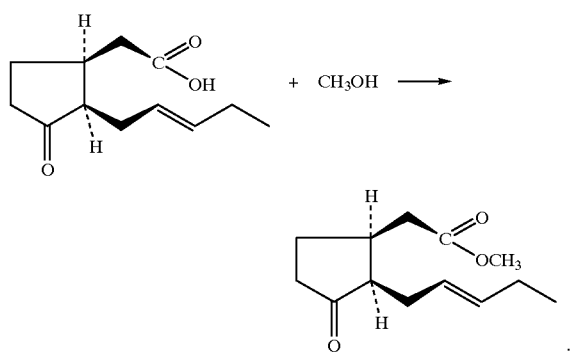

Description of Process Steps 1.0 The rush-over of the crude topped extract is carried out under best vacuum to a final pot temperature of 260C. At higher temperatures, there is thermal breakdown and some loss of vacuum. Most of the charge remains as "residue." A portion of this residue was dissolved in ethyl acetate and extracted with aqueous base. Re-acidification and GLC analysis indicated that there was no jasmonic acid left remaning in the residue.

2.0. The extract is stirred and 3 liters of 6% sodium carbonate solution to neutralize the sodium jasmonate. The pH is adjusted to 9.

3.0. The basic solution is extracted three times with hexane. This removes non-acidic impurities as well as significant sulfurous odor bodies. At lower pH, more material is removed.

The hexane extract contains approximately 160 grams of organic material. The major comonent is identified as a lactone having the structure:

This lactone is derived from the alcohol according to the reaction:

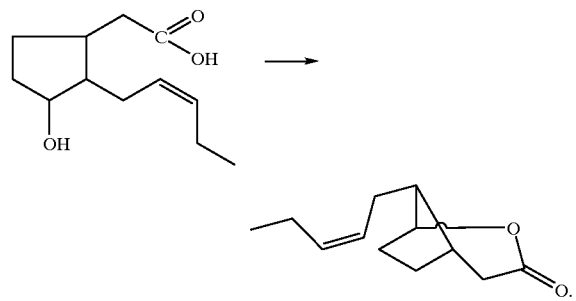

4.0. Approximately 225 grams of 85% phosphoric acid is required to adjust the acidity to pH=2.

5.0 N asm onic acid having the structures:

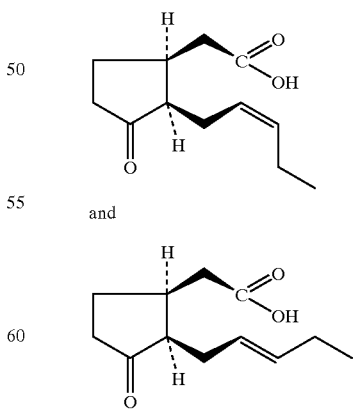

and is charged to an autoclave along with 4 times its weight of natural methanol. The autoclave is sealed and operated for a period of 12 hours at 150° C. The final composition

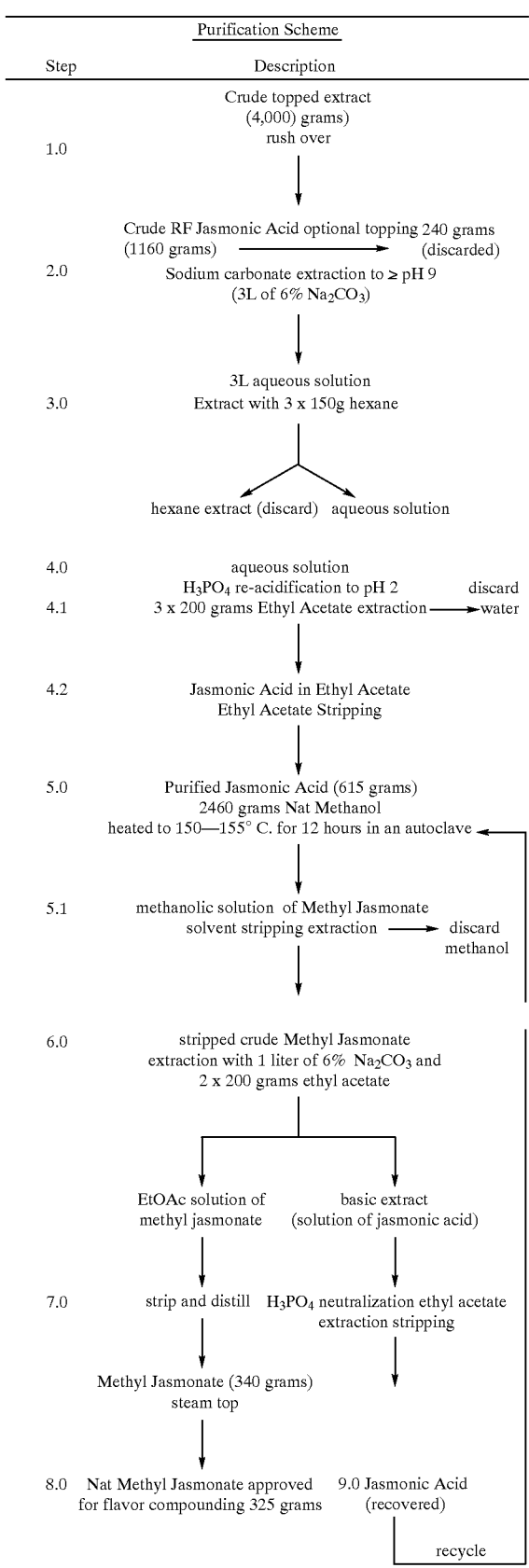

is approximately 70:30 (weight:weight) methyl jasmonate:jasmonic acid. The autoclave pressure is 220 psig.

6.0 The autoclave is opened and the methanol stripped from the resulting product.

The pH of the product is adjusted to 9.

7.0 Ethyl acetate is used to extract the resulting methyl jasmonate. The ethyl acetate is stripped at a temperature below 60° C. at atmospheric pressure. The resulting methyl jasmonate is then fractionally distilled, using a 12 inch×1.5 inch Goodloe packed column. The first fraction is distilled at a reflux ratio of 4:1, and the remainder of the fractions are distilled at reflux ratio of 1:1. The conditions of distillation are: 125° C.; vapor temperature at 1 mm/Hg pressure.

8.0 The methyl jasmonate is redistilled at a reflux ratio of 4:1 at 125° C. and 1 mm/Hg pressure.

EXAMPLE XVI

A white chocolate raspberry flavor was prepared for addition to nonfat yogurt containing aspartame.

The following flavor composition was prepared:

| Ingredients | Parts by Weight |
| --- | --- |
| Jasmonic acid prepared according to Example VI | 15 |
| Natural cocoa extract | 28 |
| Natural raspberry extract | 30 |
| 3-Phenyl-4-pentenal | 8 |

At the rate of 8 ppm, the above-mentioned mixture was added to natural nonfat yogurt containing aspartame, cultured, pasturized, grade A nonfat milk, modified cornstarch, whey protein and gelatin, and active cultures with *L. acidophilus*.

On mixing the flavor with the natural yogurt, the resulting product has a natural raspberry, fresh, "just-picked," "seedy" taste with floral topnote.

A second sample was flavored without the jasmonic acid present, and the resulting flavor did not have the "fresh-just picked-seedy" quality.

EXAMPLE XVII

Jasmine Perfume Formulation

The following mixture is prepared:

| Ingredients | Parts by Weight |
| --- | --- |
| Jasmonic acid prepared according to Example XIV | 50 |
| Methyl jasmonate product prepared according to Example XV | 50 |
| Orange oil | 20 |
| Bergamot oil | 20 |
| Neroli oil | 20 |
| γ-Methyl ionone | 20 |
| 1-Acetyl-2,5,5-trimethyl cycloheptane | 45 |

The products of Examples XIV and XV impart to this jasmine perfume formulation powerful, long lasting jasmine, floral-herbaceous aromas with sweet-herbaceous, green-woody topnotes. Accordingly, the perfume composition of Example XVII can be described as "jasmine with floral-herbaceous undertones and sweet-herbaceous, green-woody topnotes."

EXAMPLE XVIII

Preparation of Soap Compositions

100 Grams of soap chips are produced according to Example V of U.S. Pat. No. 4,058,487 issued on Nov. 5, 1997, the specification for which is incorporated herein by reference, as follows:

The sodium salt of an equal mixture of $C_{10}$–$C_{14}$ alkane sulfonate (95% active), 40 lbs, is dissolved in a mixture of 80 lbs of anhydrous isopropanol and 125 lbs of deionized water at 150° F. In this mixture is dissolved 10 lbs of partially hydrogenated coconut oil fatty acids and 15 lbs of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 lbs of water, 0.2 lbs of titanium hydroxide and 0.7 lbs of one of the perfume ingredients set forth in Table V, infra.

TABLE V

| Ingredients | Fragrance Profile |
| --- | --- |
| Jasmonic acid isomer having the structure: 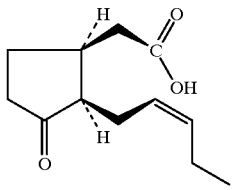 (optical rotation: +58°) | A powerful, long lasting jasmine, floral-herbaceous aroma with sweet-herbaceous, green-woody topnotes. |
| Isomer having the structure: 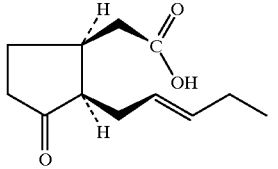 (optical rotation: +58°). | A powerful, long lasting jasmine, floral-herbaceous aroma with sweet-herbaceous, green-woody topnotes. |
| Isomer having the structure: 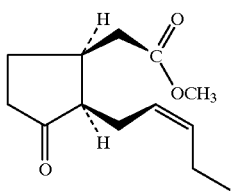 (optical rotation: +58°). | A powerful, long lasting jasmine, floral-herbaceous aroma with sweet-herbaceous, green-woody topnotes. |

TABLE V-continued

| Ingredients | Fragrance Profile |
|---|---|
| Isomer having the structure:<br><br>(optical rotation: +58°). | A powerful, long lasting jasmine, floral-herbaceous aroma with sweet-herbaceous, green-woody topnotes. |
| Perfume composition of Example XVII. | Jasmine with floral, herbaceous undertones and sweet, herbaceous, green, woody topnotes. |

EXAMPLE XIX

Preparation of Detergent Composition

A total of 100 grams of a detergent powder prepared according to U.S. Pat. No. 4,058,472 (the specification for which is incorporated by reference herein) and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table V of Example XVIII until a substantially homogeneous composition is obtained. Each of the compositions has an excellent aroma as set forth in Table V of Example XVIII.

EXAMPLE XX

Preparation of a Cosmetic Powder Composition

A cosmetic powder is prepared by mixing in a ball mill, 100 grams of talcum powder with 0.25 grams of each of the perfume materials of Table V of Example XVIII. Each of the powders has an excellent aroma as set forth in Table V of Example XVIII.

EXAMPLE XXI

Perfumed Liquid Detergent

Concentrated liquid detergents with aromas as set forth in Table V of Example XVIII are prepared by adding 0.10%, 0.15% and 0.20% of each of the ingredients set forth in Table V of Example XVIII. They are prepared by adding and homogeneously mixing the appropriate quantity of perfume substance of Table V of Example XVIII in the liquid detergent. The detergents individually possess aromas as set forth in Table V of Example XVIII, the intensity increasing with greater concentrations of perfume substance set forth in Table V of Example XVIII.

EXAMPLE XXII

Preparation of a Cologne and Handkerchief Perfume

Each of the ingredients of Table V of Example XVIII is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and defnite aromas as set forth in Table V of Example XVIII are imparted to the colognes and to the handkerchief perfimes at the several concentrations set forth above.

EXAMPLE XXIII

Preparation of Soap Compositions

100 Grams of soap chips (IVORY®, produced by the Procter & Gamble Company of Cincinnati, Ohio) are admixed with 1 gram of each of the substances set forth in Table V of Example XVIII, supra, until homogeneous compositions are heated under 3 atmospheres pressure at 180° C. for a period of 3 hours, and the resulting liquids are placed into soap molds. The resulting soap cakes, on cooling, manifest excellent aromas as set forth in Table V of Example XVIII.

EXAMPLE XXIV

Preparation of Solid Detergent Compositions

Detergents are prepared from the following ingredients according to Example I of Canadian Patent No. 1,007,948, the specification for which is incorporated by reference herein:

| Ingredients | Parts by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of each of the substances set forth in Table V of Example XVIII, supra. Each of the detergent samples has an excellent aroma as indicated in Table V of Example XVIII.

EXAMPLE XXV

Preparation of Drier-Added Fabric Softener Article

Utilizing the procedure of Example I at column 15 of U.S. Pat. No. 3,632,396, the specification for which is incorporated by reference herein, a non-woven cloth substrate useful as a drier-added fabric softening article of manufacture is prepared wherein the substrate, substrate coating, outer coating and the perfume material are as follows:

1. a water "dissolvable" paper ("Dissolvo Paper") as the substrate;
2. ADOGEN® 448 (melting point about 140° F.) as the first substrate coating; and
3. an outer coating having the following formulation (melting point about 150° F.):
    57% $C_{20}$–$C_{22}$ HAPS;
    22% isopropyl alcohol;
    20% antistatic agent; and
    1% of one of the perfumery substances set forth in Table V of Example XVIII, supra.

Fabric softening compositions containing the substances as set forth in Table V of Example XVIII, supra, essentially consist of a substrate having a weight of about 3 grams per 100 square inches; a substrate coating weighing about 1.85 grams per 100 square inches of substrate; and an outer coating weighing about, 1.5 grams per 100 square inches of substrate are prepared, thereby providing a total aromatized substrate and outer coating weight ratio of about 1:1 by weight of the substrate.

The aromas as set forth in Table V of Example XVIII supra, are imparted in a pleasant manner to the headspace in a drier on operation thereof, using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396, acting as fabric softening articles in said U.S. Pat. No. 3,632,396, may be perfumed in their outer coating with from 0.25% up to 5% by weight of each of the perfiuming substances of Table V of Example XVIII, supra.

EXAMPLE XXVI

Hair Preparation

A "soft-feel, good-hold" hair spray is produced containing the following ingredients:

| Ingredients | Parts by Weight |
| --- | --- |
| Polyvinylpyrollidone/vinyl acetate "E-735 Copolymer" manufactured by the GAF Corporation of New York, NY | 4.00 |
| Anhydrous ethanol | 70.90 |
| Dioctyl sebecate | 0.05 |
| Benzyl alcohol | 0.05 |
| "Propellant A-46" manufactured by the GAF Corporation of New York, NY | 24.95 |
| Fragrance ingredient as set forth in Table V of Example XVIII, supra | 0.05 |

The PVP/VA copolymers are first dissolved in alcohol and all other ingredients are added until uniform. The propellant is then pressurized and used as an aerosol. The resulting hair sprays each have pleasant aromas as set forth in Table V of Example XVIII, supra.

EXAMPLE XXVII

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table V of Example XVIII, supra, are added at the level of 0.25% as set forth in the table in said Example I of U.S. Pat. No. 4,193,888, yielding an aroma on using said cleanser in ordinary circumstances which is quite pleasant and described in Table V of Example XVIII, supra.

EXAMPLE XXVIII

A fabric softening article prepared substantially as set forth in Example VIII of Canadian Patent No. 1,069,260, the specification for which is incorporated by reference herein, is prepared containing 0.21% by weight of a perfuming substance as set forth in Table V of Example XVIII supra, and yielding, on use in a drier, a faint aroma as set forth in Table V of Example XVIII, supra.

EXAMPLE XXIX

Tobacco Flavor Formulations

Cigarettes are produced using the following formulations:

| Ingredients | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| $H_2O$ | 5.3 |

At the rate of 0.2%, the following tobacco formulation is applied to all of the cigarettes produced with the above tobacco formulation:

| Ingredients | Parts by Weight |
| --- | --- |
| Ethyl butyrate | 50 |
| Ethyl valerate | 50 |
| Maltol | 20 |
| Cocoa extract | 20 |
| Coffee extract | 20 |
| Ethyl alcohol (95%) | 45 |
| $H_2O$ | 41.900 |

To portions of 50% of the cigarettes at levels of 10 and 20 ppm, the jasmonic acid-containing composition of Example VI is added. These cigarettes are hereinafter called "experimental" cigarettes. The cigarettes without the jasmonic acid composition are hereinafter called "control" cigarettes. The control and experimental cigarettes are then evaluated by paired comparison and the results are as follows:

(a) in aroma, the experimental cigarettes are all found to be more aromatic with Turkish tobacco-like nuances; and (b) in smoke flavor, the experimental cigarettes are all found to be more aromatic, more sweet with Turkish tobacco, oriental-like nuances than the control cigarettes.

The experimental cigarettes containing the mixture of jasmonic acids are found to be fruity and floral and have pleasant, aesthetically pleasing fruity and floral notes, in addition.

What is claimed is:

1. A process for the manufacture of food flavor acceptable jasmonic acid in relatively high yield of from 1–2 grams per liter, containing at least 5% of a "cis" isomer having a structure selected from the group consisting of:

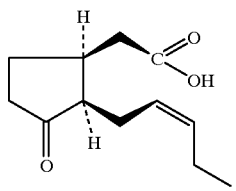

and

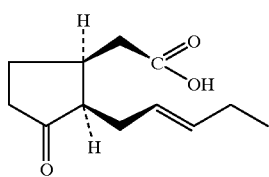

and a maximum of 95% by weight of at least one of the isomers having a structure selected from the group consisting of:

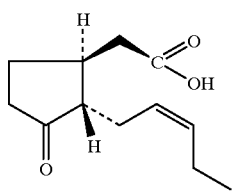

and

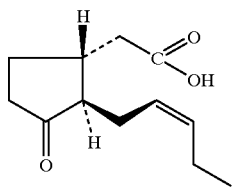

which comprises the steps of (i) cultivation under aerobic conditions of a strain of *Diplodia gossypina* organism selected from the group consisting of:

(a) *Diplodia gossypina* ATCC 10936;

(b) *Diplodia gossypina* ATCC 20575;

(c) *Diplodia gossypina* NRRL 25011; and (d) *Diplodia gossypina* ATCC 36037 in a nutrient medium containing an assimilable source of carbon and an assimilable source of nitrogen followed by (ii) isolation of the jasmonic acid product from the culture medium.

2. The process of claim 1 wherein the compound 10-oxo-trans-8-decenoic acid having the structure:

is intimately admixed in the nutrient medium in an amount of from about 0.7 up to about 10 ppm by weight of the nutrient medium prior to the cultivation step.

3. The process of claim 1 wherein the cultivation takes place under aeration conditions at an aeration rate in the range of from about 0.5 V/V/M up to about 1.0 V/V/M.

4. The process of claim 2 wherein the cultivation takes place under aeration conditions at an aeration rate in the range of from about 0.5 V/V/M up to about 1.0 V/V/M.

5. The process of claim 1 wherein the nutrient medium contains from about $6\times10^{-3}$ up to about $10.5\times10^{-3}$ gram moles/liter of $[Mg^{++}]$.

6. The process of claim 5 wherein the source of the $[Mg^{++}]$ is $MgSO_4.7H_2O$ and the range of concentrations of said $MgSO_4.7H_2O$ is from about 1.5 up to about 2.5 grams per liter.

7. The process of claim 1 wherein the strain of *Diplodia gossypina* is *Diplodia gossypina* ATCC 10936.

8. The process of claim 7 wherein the compound 10-oxo-trans-8-decenoic acid having the structure:

is intimately admixed in the nutrient medium in an amount of from about 0.7 up to about 10 ppm by weight of the nutrient medium prior to the cultivation step.

9. The process of claim 7 wherein the cultivation takes place under aeration conditions at an aeration rate in the range of from about 0.5 V/V/M up to about 1.0 V/V/M.

10. The process of claim 7 wherein the nutrient medium contains from about $6\times10^{-3}$ up to about $10.5\times10^{-3}$ gram moles/liter of $[Mg^{++}]$.

11. The process of claim 2 wherein the nutrient medium contains from about $6\times10^{-3}$ up to about $10.5\times10^{-3}$ gram moles/liter of $[Mg^{++}]$.

12. The process of claim 1 wherein methyl jasmonate containing at least 25% by weight of the isomer having the structure:

is produced from the jasmonic acid by means of reaction of the resulting jasmonic acid with methyl alcohol according to the reaction:

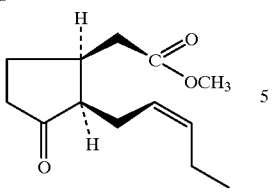
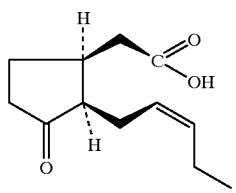

wherein the final isolation comprises the steps of:
(a) extraction of the jasmonic acid from the fermentation broth with an extraction solvent to form a jasmonic acid extract;
(b) concentration of the resulting jasmonic acid extract, whereby the extraction solvent is stripped;
(c) esterification of the resulting jasmonic acid with methyl alcohol, whereby methyl jasmonate is formed according to the reaction:

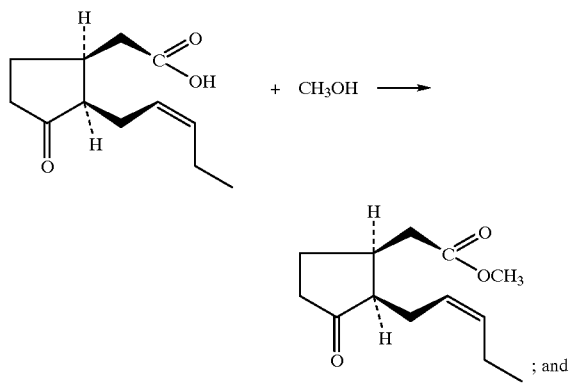

(d) concentration of the resulting methyl jasmonate.

13. The process of claim 1 wherein the jasmonic acid produced is at least 98% of the optical isomer having the structure:

having an optical rotation ($\alpha_D^{20}$) of +58° and comprising the additional steps of (iii) extraction of the resulting jasmonic acid product with a solvent in order to form a jasmonic acid product solvent extract, (iv) concentrating the resulting extract by means of solvent evaporation, thereby forming a concentrate; (v) fractionating the concentrate with silica gel in order to effect isomer separation; and (vi) collecting said 98% optical cis isomer.

14. The process of claim 1 carried out in liquid surface culture.

15. The process of claim 1 carried out in submerged liquid culture.

16. The process of claim 15 wherein the cultivation takes place under aeration conditions at an aeration rate in the range of from about 0.5 V/V/M up to about 1.0 V/V/M.

17. The process of claim 1 wherein the assimilable carbon source is glucose.

18. The process of claim 1 wherein the assimilable nitrogen source is sodium nitrate.

19. The process of claim 1 wherein the incubation time is from about 3 up to about 15 days.

20. The process of claim 1 wherein the pH range is from about 4.5 up to about 9.

21. The process of claim 20 wherein the pH of the fermentation broth is 6.

22. The process of claim 1 wherein the temperature range of reaction is from about 20° C. up to about 35° C.

23. The process of claim 1 wherein the temperature range of the fermentation is from about 25° C. up to about 32° C.

* * * * *